(12) United States Patent
Kehler et al.

(10) Patent No.: US 7,534,791 B2
(45) Date of Patent: May 19, 2009

(54) BENZO[B]FURANE AND BENZO[B]THIOPHENE DERIVATIVES

(75) Inventors: Jan Kehler, Lyngby (DK); Karsten Juhl, Greve (DK); Morten Bang Norgaard, Lyngby (DK)

(73) Assignee: H. Lundbeck A/S, Valby-Copenhagen (DK)

( * ) Notice: Subject to any disclaimer, the term of this patent is extended or adjusted under 35 U.S.C. 154(b) by 14 days.

(21) Appl. No.: 11/452,823

(22) Filed: Jun. 14, 2006

(65) Prior Publication Data

US 2006/0287386 A1    Dec. 21, 2006

(30) Foreign Application Priority Data

Jun. 17, 2005 (DK) ............................... 2005 00895

(51) Int. Cl.
*A61K 31/5377* (2006.01)
*A61K 31/38* (2006.01)
*C07D 413/02* (2006.01)
*C07D 333/54* (2006.01)

(52) U.S. Cl. .................... 514/231.5; 514/443; 544/145; 549/49; 549/52

(58) Field of Classification Search .............. 514/443, 514/231.5; 549/49, 52; 544/145
See application file for complete search history.

(56) References Cited

U.S. PATENT DOCUMENTS

| | | | |
|---|---|---|---|
| 3,803,143 | A | 4/1974 | Tanaka et al. |
| 4,018,830 | A | 4/1977 | Christy et al. |
| 4,055,665 | A | 10/1977 | Christy et al. |
| 4,056,632 | A | 11/1977 | Mehta et al. |
| 4,198,417 | A | 4/1980 | Ong et al. |
| 4,241,071 | A | 12/1980 | Martin et al. |
| 5,095,039 | A | 3/1992 | Mehta et al. |
| 5,945,425 | A | 8/1999 | Moormann et al. |
| 6,410,736 | B1 | 6/2002 | Howard et al. |
| 6,436,938 | B1 | 8/2002 | Howard et al. |
| 6,455,738 | B1 | 9/2002 | Dubac et al. |
| 6,509,340 | B1 | 1/2003 | Van Amsterdam et al. |
| 6,596,741 | B2 | 7/2003 | Howard et al. |
| 6,906,078 | B2 | 6/2005 | Moorman et al. |
| 7,189,501 | B2 | 3/2007 | Makuta et al. |
| 7,199,147 | B2 | 4/2007 | Imazaki et al. |
| 7,217,732 | B2 | 5/2007 | Kozlowski et al. |
| 7,229,751 | B2 | 6/2007 | Kimura et al. |
| 7,247,651 | B2 | 7/2007 | Madera et al. |
| 2002/0173524 | A1 | 11/2002 | Collins et al. |
| 2003/0187023 | A1 | 10/2003 | Kubo et al. |
| 2003/0207894 | A1 | 11/2003 | Theodoridis et al. |
| 2004/0009959 | A1 | 1/2004 | Potter et al. |
| 2004/0014774 | A1 | 1/2004 | Myers et al. |
| 2004/0023010 | A1 | 2/2004 | Bulovic et al. |
| 2004/0039035 | A1 | 2/2004 | Collins et al. |
| 2004/0072844 | A1 | 4/2004 | Madera et al. |
| 2004/0077854 | A1 | 4/2004 | Halazy et al. |
| 2004/0132778 | A1 | 7/2004 | Lacadie et al. |
| 2004/0137389 | A1 | 7/2004 | Fukui et al. |
| 2004/0176426 | A1 | 9/2004 | Houze et al. |
| 2004/0186148 | A1 | 9/2004 | Shankar et al. |
| 2004/0192664 | A1 | 9/2004 | Kunz et al. |
| 2004/0204451 | A1 | 10/2004 | Lacadie et al. |
| 2004/0209936 | A1 | 10/2004 | Bratton et al. |
| 2004/0220237 | A1 | 11/2004 | Fu et al. |
| 2004/0266732 | A1 | 12/2004 | Galvez et al. |
| 2005/0107599 | A1 | 5/2005 | Makioka et al. |
| 2005/0123501 | A1 | 6/2005 | Lewis |
| 2005/0136065 | A1 | 6/2005 | Valiante, Jr. |
| 2005/0152859 | A1 | 7/2005 | Dooley et al. |
| 2005/0153980 | A1 | 7/2005 | Schadt, Jr. et al. |
| 2005/0159556 | A1 | 7/2005 | Lewis et al. |
| 2005/0189519 | A1 | 9/2005 | Gothe et al. |
| 2005/0206994 | A1 | 9/2005 | Kokeguchi et al. |
| 2005/0228020 | A1 | 10/2005 | Miyamoto et al. |
| 2005/0238992 | A1 | 10/2005 | Kodama |
| 2005/0250794 | A1 | 11/2005 | Napper et al. |
| 2005/0261298 | A1 | 11/2005 | Solow-Cordero et al. |
| 2005/0282861 | A1 | 12/2005 | Friary et al. |
| 2006/0030593 | A1 | 2/2006 | Bernotas et al. |
| 2006/0069203 | A1 | 3/2006 | Lewis et al. |
| 2006/0135540 | A1 | 6/2006 | Lin et al. |
| 2006/0141286 | A1 | 6/2006 | Tada et al. |
| 2006/0148801 | A1 | 7/2006 | Hsieh et al. |
| 2006/0216546 | A1 | 9/2006 | Tada |
| 2006/0276440 | A1 | 12/2006 | An et al. |
| 2006/0287382 | A1 | 12/2006 | Kehler et al. |
| 2007/0004923 | A1 | 1/2007 | Kobayashi et al. |
| 2007/0054904 | A1 | 3/2007 | Knolle et al. |
| 2007/0060595 | A1 | 3/2007 | Yoshizawa et al. |

FOREIGN PATENT DOCUMENTS

EP    0 273 199 A2    7/1988

(Continued)

OTHER PUBLICATIONS

Mitra et al., Journal of Scientific & Industrial Resaerch, (1957), 16B, p. 348-54 , Abstract and STN search report.*
Hawkins et al., Journal of the Chemical Society, Perkin Transactions 1: Organic and Bio-Organic Chemistry (1972-1999), (1979), (12), 3207-10.*
Axford, L., et al. "Bicyclo[2.2.1]heptanes as Novel Triple Re-uptake inhibitors for the Treatment of Depression", Bioorganic & Medicinal Chemistry Letters, 2003, pp. 3277-3280, vol. 13.
Edmond, P., et al. "Substituted Diphenyl Sulfides as Selective Serotonin Transporter Ligands: Synthesis and In Vitro Evaluation", J. Med. Chem., 2002, pp. 1253-1258, vol. 45.

(Continued)

*Primary Examiner*—Rei-Tsang Shiao
*Assistant Examiner*—Yong Chu
(74) *Attorney, Agent, or Firm*—Stephen G. Kalinchak; Margaret M. Buck

(57) ABSTRACT

The present invention relates to benzo[b]furane and benzo[b]thiophene derivatives of the general formula IV as the free base or salts thereof and their use.

18 Claims, No Drawings

FOREIGN PATENT DOCUMENTS

| | | |
|---|---|---|
| EP | 0 396 827 A1 | 11/1990 |
| EP | 0 402 097 A1 | 12/1990 |
| EP | 0 755 923 A1 | 1/1997 |
| EP | 0 814 084 A1 | 12/1997 |
| EP | 0 921 124 A1 | 6/1999 |
| EP | 1 793 272 A1 | 6/2007 |
| WO | WO 93/11106 A1 | 6/1993 |
| WO | WO 93/12080 | 6/1993 |
| WO | WO 94/14770 A1 | 7/1994 |
| WO | WO 97/17325 | 5/1997 |
| WO | WO 97/17352 A1 | 5/1997 |
| WO | WO 97/48698 A1 | 12/1997 |
| WO | WO 98/08817 | 3/1998 |
| WO | WO 00/59878 | 10/2000 |
| WO | WO 00/66537 | 11/2000 |
| WO | WO 01/10842 A2 | 2/2001 |
| WO | WO 01/27068 A1 | 4/2001 |
| WO | WO 01/49667 A1 | 7/2001 |
| WO | WO 01/49678 A1 | 7/2001 |
| WO | WO 01/49679 A1 | 7/2001 |
| WO | WO 02/40024 A1 | 5/2002 |
| WO | WO 02/062766 A2 | 8/2002 |
| WO | WO 02/098857 A1 | 12/2002 |
| WO | WO 03/029232 A1 | 4/2003 |
| WO | WO 03/055873 A1 | 7/2003 |
| WO | WO 2005/061455 A1 | 7/2005 |
| WO | WO 2006/006172 A2 | 1/2006 |
| WO | WO 2006/007843 A1 | 1/2006 |
| WO | WO 2006/018850 A2 | 2/2006 |
| WO | WO 2006/038741 A1 | 4/2006 |
| WO | WO 2006/063606 A1 | 6/2006 |
| WO | WO 2006/098380 A1 | 9/2006 |

OTHER PUBLICATIONS

Hawkins, D.G., et al. "Competitive Cyclisation of Singlet and Triplet Nitrenes. Part 7. Reaction Pathways of 2-Azidophenyl Benzothienyl Azides", Journal of the Chemical Society, Perkin Transactions I: Organic and Bio-Organic Chemistry, 1979, pp. 3207-3210, No. 12.

Jackson, A., et al. "Electrophilic Substitution in Indoles Part 16 1,2 The Formation of Indolobenzothiazines and Indolobenzothiazepines by Intramolecular Cyclisation of (o-Nitrophenylthio)indoles", J. Chem. Res. Miniprint, 1988, pp. 2017-2063, vol. 9.

Jilek, J., et al. "Potential Antidepressants: 2-(Methoxy- and Hydroxy-Phenylthio)Benzylamines as Selective Inhibitors of 5-Hydroxytryptamine Re-Uptake in the Brain", Collect. Czech. Chem. Commun., 1989, pp. 3294-3338, vol. 54.

Martin, L., et al. "Synthesis of Spiro[isobenzofuran-1(3H),4'-piperidines] as Potential Central Nervous System Agents. 5. Conformationally Mobile Analogues Derived by Furan Ring Opening", J. Med. Chem., 1979, pp. 1347-1354, vol. 22, No. 11.

Oya, S., et al. "A New Single-Photon Emission Computed Tomography Imaging Agent for Serotonin Transporters: [123I] IDAM, 5-Iodo-2-((2-(((dimethylamino)methyl)-phenyl)thio)benzyl Alcohol", J. Med. Chem., 1999, pp. 333-335, vol. 42 (3).

Oya, S., et al. "New PET Imaging Agent for the Serotonin Transporter: [18F]ACF (2-[(2-Amino-4-chloro-5-fluorophenyl)thio]-N,N-dimethyl-benzenmethanamine)", J. Med. Chem., 2002, pp. 4716-4723, vol. 45.

Ragno, R., et al. "Docking and 3-D QSAR Studies on Indolyl Aryl Sulfones. Binding Mode Exploration at the HIV-1 Reverse Transcriptase Non-Nucleoside Binding Site and Design of Highly Active N-(2-Hydroxyethyl)carboxamide and N-(2-Hydroxyethyl)carbohydrazide Derivatives", J. Med. Chem., 2005, pp. 213-223, vol. 48.

Silvestri, R., et al. "Novel Indolyl Aryl Sulfones Active against HIV-1 Carrying NNRTI Resistance Mutations: Synthesis and SAR Studies", J. Med. Chemistry, 2003, pp. 2482-2493, vol. 46.

Sindelar, K., et al. "Potential Antidepressants and Inhibitors of 5-Hydroxy-Tryptamine and Noradrenaline Re-Uptake in the Brain: N,N-Dimethyl-(Arylthio)Thenylamines and N,N-Dimethyl-2-(Thienylthio) Benzylamines", Collect. Czech. Chem. Commun., 1991, pp. 449-458, vol. 56.

A. Burger, "Isosterism and Bioisosterism in drug design". Prog. Drug Res. 1991, 37:287-371.

Sejberg, J. Synth[e]sis of 3- and 2-phenylsulfanyl-1H-indole [thesis] (English Translation). Lyngby (Denmark): Technical University of Denmark; Jan. 21, 2003. 102 pages (Tables 6, 7 and 8 are attached at the end of the document). Available from: Technical University of Denmark, Lyngby, DK; d991811.

* cited by examiner

BENZO[B]FURANE AND BENZO[B]THIOPHENE DERIVATIVES

This application claims foreign priority under 35 U.S.C. § 119(a)-(d) of Danish Patent Application No. PA200500895, filed Jun. 17, 2005, the contents of which is hereby incorporated by reference into the subject application.

FIELD OF THE INVENTION

The present invention relates to compounds of formula IV and the medical use thereof e.g. in the treatment of affective disorders, pain disorders, attention deficit hyperactivity disorder (ADHD) and stress urinary incontinence.

BACKGROUND OF THE INVENTION

The majority of currently available antidepressants can be classified in 3 classes:
1. monoamine oxidase inhibitors (MAOIs),
2. biogenic amine neurotransmitter [serotonin (5-HT), norepinephrine (NE) and dopamine (DA)] transporter reuptake blockers, and
3. modulators, especially blockers of one or more of the 5-HT and/or NE receptors.

Since depression is associated with a relative deficiency of the biogenic amines, the use of 5-HT and/or NE-receptor blockers (i.e. 5-HT and or NE-antagonist's) have not proven very successful in the treatment of depression and anxiety and the preferred and currently most efficacious treatments are based on the enhancement of 5-HT and/or NE neurotransmission by blocking their reuptake back from the synaptic cleft (Slattery, D. A. et al., "The evolution of antidepressant mechanisms", *fundamental and Clinical pharmacology*, 2004, 18, 1-21; Schloss, P. et al, "new insights into the mechanism of antidepressant therapy", *Pharmacology and therapeutics*, 2004, 102, 47-60).

Selective serotonin reuptake inhibitors (hereinafter referred to as SSRIs) have become first choice therapeutics in the treatment of depression, certain forms of anxiety and social phobias, because they generally are effective, well tolerated and have a favourable safety profile compared to the classic tricyclic antidepressants. Drugs claimed to be SSRIs are for example fluoxetine, sertraline and paroxetine.

However, clinical studies on depression indicate that non-response to the known SSRIs is substantial, up to 30%. Another, often neglected, factor in the treatment of depression is the delay in the onset of the therapeutic effect of the SSRIs. Sometimes symptoms even worsen during the first weeks of treatment. Furthermore, sexual dysfunction is generally a side effect common to SSRIs. Accordingly, there is a desire for the development of compounds capable of improving the treatment of depression and other diseases related to malfunctioning of serotonin.

Dual re-uptake inhibitors providing the combined effect of 5-HT reuptake inhibition and NE (norepinephrine is also named noradrenaline, NA) reuptake inhibition on depression is explored in clinical studies of compounds such as Duloxetine (Wong, "Duloxetine (LY-248686): an inhibitor of serotonin and noradrenaline uptake and an antidepressant drug candidate", *Expert Opinion on Investigational Drugs*, 1998, 7, 10, 1691-1699) and Venlafaxine (Khan-A et al, 30 "Venlafaxine in depressed outpatients", *Psychopharmacology Bulletin*, 1991, 27, 141-144). Compounds having such dual effect are also named SNRIs, "serotonin and noradrenaline reuptake inhibitors", or NSRIs, "noradrenaline and serotonin reuptake inhibitors".

Since treatment with the selective NE reuptake inhibitor reboxetine has been shown to stimulate 5-HT neurons and mediate the release of 5-HT in the brain (Svensson, T. et al, *J. Neural Transmission*, 2004, 111, 127) there might be a synergistic advantage using SNRI's in the treatment of depression or anxiety.

The use of SNRI's have been shown in clinical studies to have a beneficial effect on pain (e.g. Fibromyalgia syndrome, overall pain, back pain, shoulder pain, headache, pain while awake and during daily activities) and especially pain associated with depression (Berk, M. *Expert Rev. Neurotherapeutics* 2003, 3, 47-451; Fishbain, D. A., et al. "Evidence-based data from animal and human experimental studies on pain relief with antidepressants: A structured review" Pain Medicine 2000 1:310-316).

SNRI's have also been shown in clinical studies to have a beneficial effect in attention deficit hyperactivity disorder (ADHD) (N. M. Mukaddes; Venlafaxine in attention deficit hyperactivity disorder, European Neuropsychopharmacology, Volume 12, Supplement 3, October 2002, Page 421).

Furthermore, SNRI's have been shown to be effective for the treatment of stress urinary incontinence (Dmochowski R. R. et al. "Duloxetine versus placebo for the treatment of North American women with stress urinary incontinence", Journal of Urology 2003, 170:4, 1259-1263.)

Naranjo, C. et al. "The role of the brain reward system in depression" *Prog. Neuro-Psychopharmacol. Biol. Psychiatry* 2001, 25, 781-823 discloses clinical and preclinical findings of links between lack of extra cellular dopamine in the mesocorticolimbic system and anhedonia, which is one of the main symptoms of depression.

Wellbutrin (bupropion) which has DA re-uptake activity in vitro and in vivo, shows antidepressant efficacy. Other combination studies have indicated that addition of some affinity at the DA uptake site may have some clinical benefit (Nelson, J. C. *J. Clin. Psychiatry* 1998, 59, 65; Masand, P. S. et al. *Depression Anxiety* 1998, 7, 89; Bodkin, J. A et al. *J. Clin. Psychiatry* 1997, 58, 137).

Axford L. et al. (2003, *Bioorganic & Medical Chemistry Letters*, 13, 3277-3280: "Bicyclo[2.2.1.]heptanes as novel triple re-uptake inhibitors for the treatment of depression") describe the development of triple 5-HT, NE and DA re-uptake inhibitors for treatment of depression. The combination of an SSRI and a norepinephrine and dopamine reuptake inhibitor, has been shown to have better efficacy in SSRI-non-responders (Lam R. W. et al. "Citalopram and Bupropion-SR: Combining Versus Switching in Patients With Treatment-Resistant Depression." *J. Clin. Psychiatry* 2004, 65, 337-340).

There is clinical evidence suggesting that the combination of an SSRI and a norepinephrine and dopamine reuptake inhibitor induces less sexual dysfunction, than treatment with SSRI's alone (Kennedy S. H. et al. "Combining Bupropion SR With Venlafaxine, Paroxetine, or Duloxetine: A Preliminary Report on Pharmacokinetic, Therapeutic, and Sexual Dysfunction Effects" *J. Clin. Psychiatry* 2002, 63, 181-186).

Diphenyl sulphides of formula I and variations thereof have been disclosed as serotonin re-uptake inhibitors and have been suggested for use in treatment of depression, cf. e.g. WO03029232(A1).

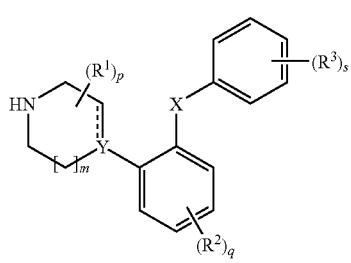

formula I

Diphenyl sulphides of formula II and variations thereof have been disclosed as serotonin re-uptake inhibitors and have been suggested for use in treatment of depression, cf. e.g. U.S. Pat. Nos. 5,095,039, 4,056,632, EP 396827 A1 and WO 9312080. EP 402097 describes halogen substituted diphenylsulfides claimed to be selective serotonin inhibitors for treatment of depression. Likewise WO 9717325 disclose derivatives of N,N-dimethyl-2-(arylthio)benzylamine claimed to be selective serotonin transport inhibitors and suggest their use as antidepressants. J. Jilek et al., *Collect. Czeck Chem. Commun.* 1989, 54, 3294-3338 also discloses various derivatives of diphenyl sulphides, "phenyl-thio-benzylamines" as antidepressants. Furthermore, diphenyl sulphides are also disclosed in U.S. Pat. No. 3,803,143 and claimed useful as antidepressant.

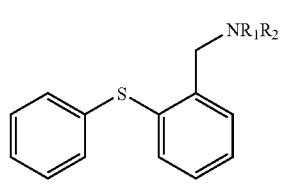

formula II

K. Sindelar et al., (K. Sindelar et al. *Collect. Czeck Chem. Commun.* 1991, 56, 449-458) disclose compounds of formula III with test for selectivity as 5-HT re-uptake inhibitor and NA re-uptake inhibitor, respectively, for use as antidepressants.

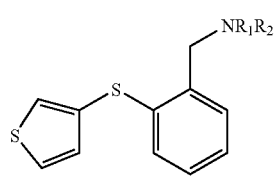

formula III

The above-mentioned references do not disclose compounds comprising an benzo[b]furane or benzo[b]thiophene group like the compounds of the present invention.

The present invention provides benzo[b]furane and benzo[b]thiophene derivatives of formula IV which are serotonin reuptake inhibitors. A particular aspect of the invention provides compounds possessing the combined effect of serotonin reuptake inhibition and norepinephrine reuptake inhibition. Another particular aspect of the invention provides compounds possessing the combined effect of serotonin reuptake inhibition and dopamine reuptake inhibition. Furthermore, some of the compounds are also triple 5-HT, NE and DA re-uptake inhibitors.

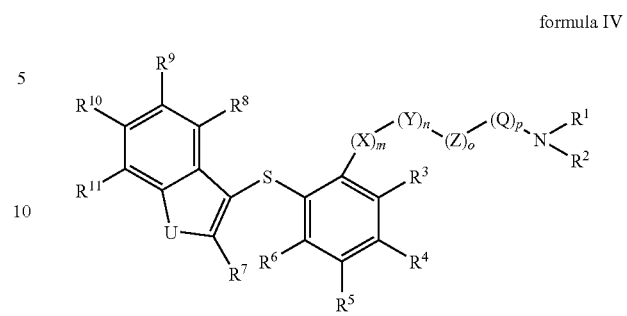

formula IV

SUMMARY OF THE INVENTION

One object of the invention is the provision of compounds, which are serotonin reuptake inhibitors. Another object of the invention is the provision of compounds, which are both serotonin reuptake inhibitors and noradrenaline reuptake inhibitors. Yet another object of the invention is the provision of compounds, which are both serotonin reuptake inhibitors and dopamine reuptake inhibitors. Yet another object of the invention is the provision of compounds, which are serotonin reuptake inhibitors, noradrenaline reuptake inhibitors and dopamine reuptake inhibitors.

The compounds of the invention are substituted benzo[b]furane and benzo[b]thiophene derivatives of the general formula IV as the free base or salts thereof.

The invention provides a compound according to the above for use as a medicament.

The invention provides a pharmaceutical composition comprising a compound according to the above and at least one pharmaceutically acceptable carrier or diluent.

The invention provides the use of a compound according to the above for the preparation of a pharmaceutical composition for the treatment of affective disorders, pain disorders, ADHD and stress urinary incontinence.

The invention furthermore concerns the use of a compound according to the above in a method of treatment of affective disorders, pain disorders, ADHD and stress urinary incontinence.

Definition of Substituents

The term heteroatom refers to a nitrogen, oxygen or sulphur atom.

Halo means halogen. Halogen means fluoro, chloro, bromo or iodo.

The expression "$C_{1-6}$-alk(en/yn)yl" means a $C_{1-6}$-alkyl, a $C_{2-6}$-alkenyl or a $C_{2-6}$-alkynyl group. The term "$C_{1-6}$-alkyl" refers to a branched or unbranched alkyl group having from one to six carbon atoms inclusive, including but not limited to methyl, ethyl, 1-propyl, 2-propyl, 1-butyl, 2-butyl, 2-methyl-2-propyl and 2-methyl-1-propyl. The term "$C_{2-6}$-alkenyl" refers to a branched or unbranched alkenyl group having from two to six carbon atoms, including one double bond, including but not limited to ethenyl, propenyl, and butenyl. The term "$C_{2-6}$-alkynyl" refers to a branched or unbranched alkynyl group having from two to six carbon atoms, including one triple bond, including but not limited to ethynyl, propynyl and butynyl.

The expression "$C_{3-8}$-cycloalk(en)yl" means a $C_{3-8}$-cycloalkyl or a $C_{3-8}$-cycloalkenyl group. The term "$C_{3-8}$-cycloalkyl" designates a monocyclic or bicyclic carbocycle having three to eight C-atoms, including but not limited to cyclopropyl, cyclopentyl, and cyclohexyl. The term "$C_{3-8}$-cycloalkenyl" designates a monocyclic or bicyclic carbocycle having three to eight C-atoms and one double bond, including but not limited to cyclopropenyl, cyclopentenyl and cyclohexenyl.

In the expression "$C_{3-8}$-cycloalk(en)yl-$C_{1-6}$-alk(en/yn)yl", "$C_{1-6}$-alk(en/yn)ylamino", "di-($C_{1-6}$-alk(en/yn)yl)amino", "$C_{3-8}$-cycloalk(en)ylamino", "$C_{3-8}$-cycloalk(en)yl-$C_{1-6}$-alk(en/yn)ylamino" "$C_{1-6}$-alk(en/yn)yloxy", "$C_{3-8}$-cycloalk(en)yloxy", "$C_{3-8}$-cycloalk(en)yl-$C_{1-6}$-alk(en/yn)yloxy" "$C_{1-6}$-alk(en/yn)ylsulfanyl", "$C_{3-8}$-cycloalk(en)ylsulfanyl", "$C_{3-8}$-cycloalk(en)yl-$C_{1-6}$-alk(en/yn)ylsulfanyl", "halo-$C_{1-6}$-alk(en/yn)yl", "halo-$C_{3-8}$-cycloalk(en)yl", "halo-$C_{3-8}$-cycloalk(en)yl-$C_{1-6}$-alk(en/yn)yl", the terms "amino", "$C_{3-8}$-cycloalk(en)yl", "$C_{1-6}$-alk(en/yn)yl", "$C_{1-6}$-alk(en)yl" and "halo" are as defined above.

The term "$R^1$ and $R^2$ together with the nitrogen form a 4-7 membered ring containing zero or one double bond, optionally said ring in addition to said nitrogen comprises one further heteroatom selected from oxygen and sulphur" refers to such ring systems wherein a ring is formed by the nitrogen to which $R^1$ and $R^2$ are attached and 3-6 atoms selected from 2-6 carbon atoms and 0-1 heteroatoms selected from sulphur and oxygen, said ring contains zero or one double bond. Examples of rings formed by $R^1$, $R^2$ and the nitrogen to which they are attached are pyrrolidine, piperidine, morpholine and thiomorpholine.

DESCRIPTION OF THE INVENTION

The present invention relates to the free base or a salt of the compounds represented by the general formula IV formula IV

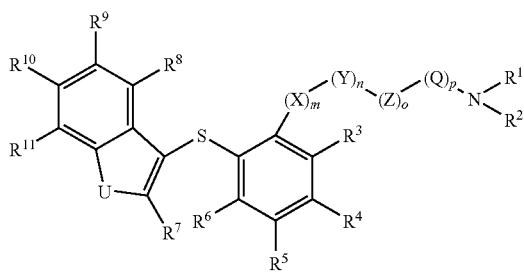

wherein
U is oxygen or sulphur;
$R^1$-$R^2$ are independently selected from the group consisting of hydrogen, $C_{1-6}$-alk(en/yn)yl, $C_{3-8}$-cycloalk(en)yl, and $C_{3-8}$-cycloalk(en)yl-$C_{1-6}$-alk(en/yn)yl; or $R^1$ and $R^2$ together with the nitrogen to which they are attached form a 4-7 membered ring containing zero or one double bond, optionally said ring in addition to said nitrogen comprises one further heteroatom selected from oxygen and sulphur;
$R^3$-$R^6$ are independently selected from the group consisting of hydrogen, halogen, cyano, $C_{1-6}$-alk(en/yn)yl, $C_{3-8}$-cycloalk(en)yl, $C_{3-8}$-cycloalk(en)yl-$C_{1-6}$-alk(en/yn)yl, halo-$C_{1-6}$-alk(en/yn)yl, halo-$C_{3-8}$-cycloalk(en)yl and halo-$C_{3-8}$-cycloalk(en)yl-$C_{1-6}$-alk(en/yn)yl;
$R^7$ is selected from the group consisting of hydrogen, $C_{1-6}$-alk(en/yn)yl, $C_{3-8}$-cycloalk(en)yl and $C_{3-8}$-cycloalk(en)yl-$C_{1-6}$-alk(en/yn)yl;
$R^8$-$R^{11}$ are independently selected from the group consisting of hydrogen, halogen, cyano, $C_{1-6}$-alk(en/yn)yl, $C_{3-8}$-cycloalk(en)yl, $C_{3-8}$-cycloalk(en)yl-$C_{1-6}$-alk(en/yn)yl, halo-$C_{1-6}$-alk(en/yn)yl, halo-$C_{3-8}$-cycloalk(en)yl, halo-$C_{3-8}$-cycloalk(en)yl-$C_{1-6}$-alk(en/yn)yl, nitro, amino, $C_{1-6}$-alk(en/yn)ylamino, di-($C_{1-6}$-alk(en/yn)yl)amino, $C_{3-8}$-cycloalk(en)ylamino, $C_{3-8}$-cycloalk(en)yl-$C_{1-6}$-alk(en/yn)ylamino, hydroxy, $C_{1-6}$-alk(en/yn)yloxy, $C_{3-8}$-cycloalk(en)yloxy, $C_{3-8}$-cycloalk(en)yl-$C_{1-6}$-alk(en/yn)yloxy, $C_{1-6}$-alk(en/yn)ylsulfanyl, $C_{3-9}$-cycloalk(en)ylsulfanyl and $C_{3-8}$-cycloalk(en)yl-$C_{1-6}$-alk(en/yn)ylsulfanyl;
m, n, o and p are independently 0 or 1;
X is selected from the group consisting of $CH_2$, $CHR^{12}$ and $CR^{13}R^{14}$;
Y is selected from the group consisting of $CH_2$, $CHR^{15}$ and $CR^{16}R^{17}$;
Z is selected from the group consisting of $CH_2$, $CHR^{18}$ and $CR^{19}R^{20}$; and
Q is selected from the group consisting of $CH_2$, $CHR^{21}$ and $CR^{22}R^{23}$;
wherein $R^{12}$-$R^{23}$ are independently selected from the group consisting of $C_{1-6}$-alk(en/yn)yl, $C_{3-8}$-cycloalk(en)yl and $C_{3-8}$-cycloalk(en)yl-$C_{1-6}$-alk(en/yn)yl;

as the free base or a salt thereof.

In one embodiment of the compound of formula IV, U is oxygen; in another embodiment of the compound of formula IV, U is sulphur.

In one embodiment of the compound of formula IV, $R^1$ and $R^2$ are independently selected from the group consisting of $C_{3-8}$-cycloalk(en)yl and $C_{3-8}$-cycloalk(en)yl-$C_{1-6}$-alk(en/yn)yl.

In a further embodiment of the compound of formula IV, $R^1$ and $R^2$ are independently selected from the group consisting of hydrogen and $C_{1-6}$-alk(en/yn)yl; or $R^1$ and $R^2$ together with the nitrogen form a 4-7 membered ring containing zero or one double bond, optionally said ring in addition to said nitrogen comprises one further heteroatom selected from oxygen and sulphur.

To further illustrate without limiting the invention an embodiment of $R^1$ is hydrogen; another embodiment of $R^1$ is $C_{1-6}$-alk(en/yn)yl such as methyl.

To further illustrate without limiting the invention an embodiment of $R^2$ is hydrogen; another embodiment of $R^2$ is $C_{1-6}$-alk(en/yn)yl such as methyl.

To further illustrate without limiting the invention, an embodiment of the compound of formula IV concerns such compounds wherein $R^1$ and $R^2$ together with the nitrogen form a 4-7 membered ring containing zero or one double bond, optionally said ring in addition to said nitrogen comprises one further heteroatom selected from oxygen and sulphur. In one embodiment said 4-7 membered ring does not contain any double bond; in another embodiment said 4-7 membered ring does contain one double bond. In one embodiment the only heteroatom contained in said 4-7 membered ring is the nitrogen to which $R^1$ and $R^2$ are attached. In another embodiment said 4-7 membered ring contains one heteroatom in addition to the nitrogen to which $R^1$ and $R^2$ are attached; in a further embodiment said heteroatom is sulphur; in a further embodiment said heteroatom is oxygen. Typically said 4-7 membered ring is selected from the group consisting of morpholine and thiomorpholine.

In a further embodiment of the compound of formula IV, $R^3$-$R^6$ are independently selected from the group consisting of cyano, $C_{3-8}$-cycloalk(en)yl, $C_{3-8}$-cycloalk(en)yl-$C_{1-6}$-alk(en/yn)yl, halo-$C_{1-6}$-alk(en/yn)yl, halo-$C_{3-8}$-cycloalk(en)yl and halo-$C_{3-8}$-cycloalk(en)yl-$C_{1-6}$-alk(en/yn)yl.

In a further embodiment of the compound of formula IV, $R^3$-$R^6$ are independently selected from the group consisting of hydrogen, halogen, cyano, $C_{1-6}$-alk(en/yn)yl, $C_{3-8}$-cycloalk(en)yl and $C_{3-8}$-cycloalk(en)yl-$C_{1-6}$-alk(en/yn)yl.

Typically, $R^3$-$R^6$ are independently selected from the group consisting of hydrogen, halogen and $C_{1-6}$-alk(en/yn)yl.

To further illustrate without limiting the invention an embodiment of $R^3$ is hydrogen.

Typically, $R^4$ is selected from the group consisting of hydrogen and $C_{1-6}$-alk(en/yn)yl. To further illustrate without limiting the invention an embodiment of $R^4$ is hydrogen; another embodiment of $R^4$ is $C_{1-6}$-alk(en/yn)yl such as methyl.

Typically, $R^5$ is selected from the group consisting of hydrogen and halogen. To further illustrate without limiting the invention an embodiment of $R^5$ is hydrogen; another embodiment of $R^5$ is halogen such as chloro.

To further illustrate without limiting the invention an embodiment of $R^6$ is hydrogen.

In a further embodiment of the compound of formula IV, $R^7$ is selected from the group consisting of $C_{3-8}$-cycloalk(en)yl and $C_{3-8}$-cycloalk(en)yl-$C_{1-6}$-alk(en/yn)yl.

Typically, $R^7$ is selected from the group consisting of hydrogen and $C_{1-6}$-alk(en/yn)yl.

To further illustrate without limiting the invention an embodiment of $R^7$ is hydrogen; another embodiment of $R^7$ is $C_{1-6}$-alk(en/yn)yl such as methyl.

In a further embodiment of the compound of formula IV, $R^8$-$R^{11}$ are independently selected from the group consisting of cyano, $C_{3-8}$-cycloalk(en)yl, $C_{3-8}$-cycloalk(en)yl-$C_{1-6}$-alk(en/yn)yl, halo-$C_{1-6}$-alk(en/yn)yl, halo-$C_{3-8}$-cycloalk(en)yl, halo-$C_{3-8}$-cycloalk(en)yl-$C_{1-6}$-alk(en/yn)yl, nitro, amino, $C_{1-6}$-alk(en/yn)ylamino, $C_{3-8}$-cycloalk(en)ylamino, $C_{3-8}$-cycloalk(en)yl-$C_{1-6}$-alk(en/yn)ylamino, $C_{3-9}$-cycloalk(en)yloxy, $C_{3-8}$-cycloalk(en)yl-$C_{1-6}$-alk(en/yn)yloxy, $C_{1-6}$-alk(en/yn)ylsulfanyl, $C_{3-8}$-cycloalk(en)ylsulfanyl and $C_{3-8}$-cycloalk(en)yl-$C_{1-6}$-alk(en/yn)ylsulfanyl.

In a further embodiment of the compound of formula IV, $R^8$-$R^{11}$ are independently selected from the group consisting of hydrogen, halogen, cyano, $C_{1-6}$-alk(en/yn)yl, $C_{3-8}$-cycloalk(en)yl, $C_{3-8}$-cycloalk(en)yl-$C_{1-6}$-alk(en/yn)yl, amino, $C_{1-6}$-alk(en/yn)ylamino, $C_{3-8}$-cycloalk(en)ylamino, $C_{3-8}$-cycloalk(en)yl-$C_{1-6}$-alk(en/yn)ylamino, di-($C_{1-6}$-alk(en/yn)yl)amino, hydroxy, $C_{1-6}$-alk(en/yn)yloxy, $C_{3-8}$-cycloalk(en)yloxy, and $C_{3-8}$-cycloalk(en)yl-$C_{1-6}$-alk(en/yn)yloxy.

Typically, $R^8$-$R^{11}$ are independently selected from the group consisting of hydrogen, halogen, $C_{1-6}$-alk(en/yn)yl, di-($C_{1-6}$-alk(en/yn)yl)amino, hydroxy and $C_{1-6}$-alk(en/yn)yloxy.

Typically, $R^8$ is selected from the group consisting of hydrogen, halogen and $C_{1-6}$-alk(en/yn)yl. To further illustrate without limiting the invention an embodiment of $R^8$ is hydrogen; another embodiment of $R^8$ is halogen such as fluoro; another embodiment of $R^8$ is $C_{1-6}$-alk(en/yn)yl such as methyl.

Typically, $R^9$ is selected from the group consisting of hydrogen, halogen, $C_{1-6}$-alk(en/yn)yl, di-($C_{1-6}$-alk(en/yn)yl)amino and hydroxy. To further illustrate without limiting the invention an embodiment of $R^9$ is hydrogen; another embodiment of $R^9$ is halogen such as fluoro or chloro; another embodiment of $R^9$ is $C_{1-6}$-alk(en/yn)yl such as methyl; another embodiment of $R^9$ is di-($C_{1-6}$-alk(en/yn)yl)amino such as dimethylamino; another embodiment of $R^9$ is hydroxy.

Typically, $R^{10}$ is selected from the group consisting of hydrogen and $C_{1-6}$-alk(en/yn)yl. To further illustrate without limiting the invention an embodiment of $R^{10}$ is hydrogen; another embodiment of $R^{10}$ is $C_{1-6}$-alk(en/yn)yl such as methyl.

Typically, $R^{11}$ is selected from the group consisting of hydrogen, $C_{1-6}$-alk(en/yn)yl and $C_{1-6}$-alk(en/yn)yloxy. To further illustrate without limiting the invention an embodiment of $R^{11}$ is hydrogen; another embodiment of $R^{11}$ is $C_{1-6}$-alk(en/yn)yl such as methyl; another embodiment of $R^{11}$ is $C_{1-6}$-alk(en/yn)yloxy such as methoxy.

In a further embodiment of the compound of formula IV, X is selected from the group consisting of $CHR^{12}$ and $CR^{13}R^{14}$, Y is selected from the group consisting of $CHR^{15}$ and $CR^{16}R^{17}$, Z is selected from the group consisting of $CHR^{18}$ and $CR^{19}R^{20}$, and Q is selected from the group consisting of $CHR^{21}$ and $CR^{22}R^{23}$.

In a further embodiment of the compound of formula IV, X, Y, Z and Q are $CH_2$.

In a further embodiment of the compound of formula IV, m+n+o+p equals to 1, 2, 3 or 4; in another embodiment of formula IV, m+n+o+p equals to 1; in another embodiment of formula IV, m+n+o+p equals to 2; in another embodiment of formula IV, m+n+o+p equals to 3; in another embodiment of formula IV, m+n+o+p equals to 4.

In a further embodiment of the compound of formula IV said compound is selected from the following list of compounds:

| Compound No | Name |
| --- | --- |
| 1 | [2-(Benzo[b]furan-3-ylsulfanyl)-benzyl]-methyl-amine |
| 2 | [2-(Benzo[b]thiophen-3-ylsulfanyl)-benzyl]-methyl-amine |
| 3 | Methyl-[2-(2-methyl-benzo[b]thiophen-3-ylsulfanyl)-benzyl]-amine |
| 4 | [2-(5-Fluoro-benzo[b]thiophen-3-ylsulfanyl)-benzyl]-methyl-amine |
| 5 | Methyl-[2-(2-methyl-benzo[b]furan-3-ylsulfanyl)-benzyl]-amine |
| 6 | Methyl-[2-(5-methyl-benzo[b]thiophen-3-ylsulfanyl)-benzyl]-amine |
| 7 | [2-(5-Chloro-benzo[b]thiophen-3-ylsulfanyl)-benzyl]-methyl-amine |
| 8 | [2-(Benzo[b]thiophen-3-ylsulfanyl)-benzyl]-dimethyl-amine |
| 9 | [2-(Benzo[b]thiophen-3-ylsulfanyl)-5-methyl-benzyl]-methyl-amine |
| 10 | [2-(Benzo[b]thiophen-3-ylsulfanyl)-4-chloro-benzyl]-methyl-amine |
| 11 | [2-(4-Fluoro-benzo[b]thiophen-3-ylsulfanyl)-benzyl]-methyl-amine |
| 12 | Dimethyl-[3-(2-methylaminomethyl-phenylsulfanyl)-benzo[b]thiophen-5-yl]-amine |
| 13 | Methyl-[2-(7-methyl-benzo[b]thiophen-3-ylsulfanyl)-benzyl]-amine |
| 14 | [2-(4,7-Dimethyl-benzo[b]thiophen-3-ylsulfanyl)-benzyl]-methyl-amine |
| 15 | 3-(2-Methylaminomethyl-phenylsulfanyl)-benzo[b]thiophen-5-ol |
| 16 | Methyl-[2-(6-methyl-benzo[b]thiophen-3-ylsulfanyl)-benzyl]-amine |
| 17 | [2-(7-Methoxy-benzo[b]thiophen-3-ylsulfanyl)-benzyl]-methyl-amine |
| 18 | {2-[2-(Benzo[b]thiophen-3-ylsulfanyl)-phenyl]-ethyl}-methyl-amine |
| 19 | {2-[2-(Benzo[b]furan-3-ylsulfanyl)-phenyl]-ethyl}-methyl-amine |
| 20 | {3-[2-(Benzo[b]thiophen-3-ylsulfanyl)-phenyl]-propyl}-methyl-amine |
| 21 | {3-[2-(Benzo[b]furan-3-ylsulfanyl)-phenyl]-propyl}-methyl-amine |
| 22 | {4-[2-(Benzo[b]thiophen-3-ylsulfanyl)-phenyl]-butyl}-methyl-amine |
| 23 | {4-[2-(Benzo[b]furan-3-ylsulfanyl)-phenyl]-butyl}-methyl-amine |
| 24 | 2-(Benzo[b]thiophen-3-ylsulfanyl)-benzylamine |

-continued

| Compound No | Name |
|---|---|
| 25 | 4-[2-(Benzo[b]thiophen-3-ylsulfanyl)-benzyl]-morpholine |
| 26 | 4-[2-(Benzo[b]thiophen-3-ylsulfanyl)-benzyl]-thiomorpholine | as the free base or a salt thereof. Each of these compounds is considered a specific embodiment and may be subjected to individual claims.

The present invention comprises the free base and salts of the compounds of the invention, typically, pharmaceutically acceptable salts. The salts of the invention include acid addition salts, metal salts, ammonium and alkylated ammonium salts.

The salts of the invention are preferably acid addition salts. The acid addition salts of the invention are preferably pharmaceutically acceptable salts of the compounds of the invention formed with non-toxic acids. Acid addition salts include salts of inorganic acids as well as organic acids. Examples of suitable inorganic acids include hydrochloric, hydrobromic, hydroiodic, phosphoric, sulfuric, sulfamic, nitric acids and the like. Examples of suitable organic acids include formic, acetic, trichloroacetic, trifluoroacetic, propionic, benzoic, cinnamic, citric, fumaric, glycolic, itaconic, lactic, methanesulfonic, maleic, malic, malonic, mandelic, oxalic, picric, pyruvic, salicylic, succinic, methane sulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, theophylline acetic acids, as well as the 8-alotheophyllines, for example 8-bromotheophylline and the like. Further examples of pharmaceutical acceptable inorganic or organic acid addition salts include the pharmaceutically acceptable salts listed in *J. Pharm. Sci.* 1977, 66, 2, which is incorporated herein by reference.

Also intended as acid addition salts are the hydrates, which the present compounds are able to form.

Examples of metal salts include lithium, sodium, potassium, magnesium salts and the like.

Examples of ammonium and alkylated ammonium salts include ammonium, methyl-, dimethyl-, trimethyl-, ethyl-, hydroxyethyl-, diethyl-, n-butyl-, sec-butyl-, tert-butyl-, tetramethylammonium salts and the like.

Further, the compounds of this invention may exist in unsolvated as well as in solvated forms with pharmaceutically acceptable solvents such as water, ethanol and the like. In general, the solvated forms are considered equivalent to the unsolvated forms for the purposes of this invention.

The compounds of the present invention may have one or more asymmetric centre and it is intended that any optical isomers (i.e. enantiomers or diastereomers), as separated, pure or partially purified optical isomers and any mixtures thereof including racemic mixtures, i.e. a mixture of stereoisomeres, are included within the scope of the invention.

Racemic forms can be resolved into the optical antipodes by known methods, for example, by separation of diastereomeric salts thereof with an optically active acid, and liberating the optically active amine compound by treatment with a base. Another method for resolving racemates into the optical antipodes is based upon chromatography on an optically active matrix. Racemic compounds of the present invention can also be resolved into their optical antipodes, e.g. by fractional crystallization. The compounds of the present invention may also be resolved by the formation of diastereomeric derivatives. Additional methods for the resolution of optical isomers, known to those skilled in the art, may be used. Such methods include those discussed by J. Jaques, A. Collet and S. Wilen in "Enantiomers, Racemates, and Resolutions", John Wiley and Sons, New York (1981). Optically active compounds can also be prepared from optically active starting materials, or by stereoselective synthesis.

Furthermore, when a double bond or a fully or partially saturated ring system is present in the molecule geometric isomers may be formed. It is intended that any geometric isomers, as separated, pure or partially purified geometric isomers or mixtures thereof are included within the scope of the invention. Likewise, molecules having a bond with restricted rotation may form geometric isomers. These are also intended to be included within the scope of the present invention.

Furthermore, some of the compounds of the present invention may exist in different tautomeric forms and it is intended that any tautomeric forms that the compounds are able to form are included within the scope of the present invention.

The invention also encompasses prodrugs of the present compounds, which on administration undergo chemical conversion by metabolic processes before becoming pharmacologically active substances. In general, such prodrugs will be functional derivatives of the compounds of the general formula IV which are readily convertible in vivo into the required compound of the formula IV. Conventional procedures for the selection and preparation of suitable prodrug derivatives are described, for example, in "Design of Prodrugs", ed. H. Bundgaard, Elsevier, 1985.

The invention also encompasses active metabolites of the present compounds.

Some compounds according to the invention inhibit the serotonin transporter and are thus serotonin reuptake inhibitors. Typically, the compounds have an in vitro uptake inhibition (IC50) of 5 µM or less, typically of 1 µM or less, preferably less than 500 nM or less than 100 nM or less than 50 nM, preferably as measured by the method described in Example 20—Measurements of "[$^3$H]-5-HT uptake into rat cortical synaptosomes".

Some compounds according to the invention inhibit the norepinephrine transporter and are thus norepinephrine reuptake inhibitors. The compounds typically have an in vitro uptake inhibition (IC50) of 5 µM or less, typically of 1 µM or less, preferably less than 500 nM, less than 100 nM or less than 50 nM, as measured by the method described in Example 20—Measurements of "[$^3$H]noradrenaline uptake into rat cortical synaptosomes".

Some compounds according to the invention inhibit the dopamine transporter and are thus dopamine reuptake inhibitors. Typically, such compounds have an in vitro uptake inhibition (IC50) of 5 µM or less, typically of 1 µM or less, preferably less than 500 nM, less than 100 nM or less than 50 nM, preferably as measured by the method described in Example 20—"Measurements of [$^3$H]dopamine uptake into rat cortical synaptosomes".

As already mentioned, the compounds according to the invention are serotonin reuptake inhibitors and they are thus considered to be applicable in the treatment of one or more of the following diseases and disorders: affective disorders, pain disorders, ADHD and stress urinary incontinence.

An embodiment concerns compounds of the invention having dual action, said compounds being serotonin reuptake inhibitors and norepinephrine reuptake inhibitors at the same time. Typically, such compounds have an in vitro uptake inhibition for the serotonin transporter which is at least 1, typically at least 5 or even more typically at least 10, 20 or 30 times higher than the in vitro uptake inhibition for the norepinephrine transporter as measured by the methods described in Example 20—"Measurements of [$^3$H]-5-HT uptake into rat cortical synaptosomes" and "Measurements of [$^3$H]noradrenaline uptake into rat cortical synaptosomes".

An embodiment concerns compounds of the invention having dual action, said compounds being serotonin reuptake inhibitors and dopamine reuptake inhibitors at the same time. Typically, such compounds have an in vitro uptake inhibition for the serotonin transporter which is at least 1, typically at least 5 or even more typically at least 10, 20 or 30 times higher than the in vitro uptake inhibition for the dopamine transporter as measured by the methods described in Example 20—"Measurements of [$^3$H]-5-HT uptake into rat cortical synaptosomes" and "Measurements of [$^3$H]dopamine uptake into rat cortical synaptosomes".

A further embodiment concerns compounds of the invention having triple action and thus being serotonin reuptake inhibitors, norepinephrine reuptake inhibitors and dopamine reuptake inhibitors.

In a further aspect the invention provides a compound of formula IV as the free base or a salt thereof for use as a medicament.

An embodiment of the invention provides a pharmaceutical composition comprising a compound of formula IV as the free base or a salt thereof and at least one pharmaceutically acceptable carrier or diluent. The composition may comprise any one of the embodiments of formula IV described above.

A further embodiment of the invention relates to the use of a compound of formula IV as the free base or a salt thereof for the preparation of a pharmaceutical composition for the treatment of a disease or disorder wherein a serotonin reuptake inhibitor is beneficial. Such pharmaceutical composition may comprise any one of the embodiments of formula IV described above.

A further embodiment of the invention relates to the use of a compound of formula IV as the free base or a salt thereof for the preparation of a pharmaceutical composition for the treatment of a disease or disorder, wherein a combined serotonin and norepinephrine reuptake inhibitor is beneficial. Such pharmaceutical composition may comprise any one of the embodiments of formula IV described above.

A further embodiment of the invention relates to the use of a compound of formula IV as the free base or a salt thereof for the preparation of a pharmaceutical composition for the treatment of a disease or disorder, wherein a combined serotonin and dopamine reuptake inhibitor is beneficial. Such pharmaceutical composition may comprise any one of the embodiments of formula IV described above.

A further embodiment of the present invention relates to the use of a compound of formula IV as the free base or a salt thereof for the preparation of a pharmaceutical composition for the treatment of a disease or disorder, wherein a combined serotonin, norepinephrine and dopamine reuptake inhibitor is beneficial. Such pharmaceutical composition may comprise any one of the embodiments of formula IV described above.

A further embodiment of the invention relates to the use of a compound of formula IV as the free base or a salt thereof for the preparation of a pharmaceutical composition for the treatment of affective disorders, pain disorders, ADHD and stress urinary incontinence.

In a further embodiment the present invention relates to the use of a compound of formula IV as the free base or a salt thereof for the preparation of a pharmaceutical composition for the treatment of affective disorders. To further illustrate without limiting the invention, the affective disorder to be treated is selected from the group consisting of depressive disorders and anxiety disorders.

A further embodiment concerns the use of a compound of formula IV as the free base or a salt thereof for the preparation of a pharmaceutical composition for the treatment of depressive disorders. Typically, the depressive disorder to be treated is selected from the group consisting of major depressive disorder, postnatal depression, dysthymia and depression associated with bipolar disorder, alzheimers, psychosis or parkinsons.

A further embodiment concerns the use of a compound of formula IV as the free base or a salt thereof for the preparation of a pharmaceutical composition for the treatment of anxiety disorders. Typically, the anxiety disorders to be treated are selected from the group consisting of general anxiety disorder, social anxiety disorder, post traumatic stress disorder, obsessive compulsive disorder, panic disorder, panic attacks, specific phobias, social phobia and agoraphobia.

In a further embodiment the present invention relates to the use of a compound of formula IV as the free base or a salt thereof for the preparation of a pharmaceutical composition for the treatment of pain disorders. To further illustrate without limiting the invention, the pain disorder to be treated is selected from the group consisting of fibromyalgia syndrome (FMS), overall pain, back pain, shoulder pain, headache as well as pain while awake and during daily activities.

In a further embodiment the present invention relates to the use of a compound of formula IV as the free base or a salt thereof for the preparation of a pharmaceutical composition for the treatment of attention deficit hyperactivity disorder.

In a further embodiment the present invention relates to the use of a compound of formula IV as the free base or a salt thereof for the preparation of a pharmaceutical composition for the treatment of stress urinary incontinence.

In a further aspect, the present invention relates to a method of preparing a compound of formula IV, comprising the nucleophilic substitution reaction of an appropriately substituted benzo[b]furane or benzo[b]thiophene and an appropriately substituted benzene sulfenyl chloride activated by an appropriate Lewis Acid.

The term "treatment" as used herein in connection with a disease or disorders includes also prevention as the case may be.

Pharmaceutical Compositions

The present invention also relates to a pharmaceutical composition. The compounds of the invention may be administered alone or in combination with pharmaceutically acceptable carriers or diluents, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 19 Edition, Gennaro, Ed., Mack Publishing Co., Easton, Pa., 1995.

The pharmaceutical compositions may be specifically formulated for administration by any suitable route such as the oral, rectal, nasal, pulmonary, topical (including buccal and sublingual), transdermal, intracisternal, intraperitoneal, vaginal and parenteral (including subcutaneous, intramuscular, intrathecal, intravenous and intradermal) route, the oral route being preferred. It will be appreciated that the preferred route will depend on the general condition and age of the subject to be treated, the nature of the condition to be treated and the active ingredient chosen.

The pharmaceutical compositions formed by combining the compound of the invention and the pharmaceutical acceptable carriers are then readily administered in a variety of dosage forms suitable for the disclosed routes of administration. The formulations may conveniently be presented in unit dosage form by methods known in the art of pharmacy.

The compounds of this invention are generally utilized as the free substance (base) or as a pharmaceutically acceptable salt thereof. One example is an acid addition salt of a compound having the utility of a free base. When a compound of the invention contains a free base such salts are prepared in a conventional manner by treating a solution or suspension of a free base of the invention with a chemical equivalent of a pharmaceutically acceptable acid. Representative examples are mentioned above.

Pharmaceutical compositions for oral administration may be solid or liquid. Solid dosage forms for oral administration include e.g. capsules, tablets, dragees, pills, lozenges, powders, granules and tablette e.g. placed in a hard gelatine capsule in powder or pellet form or e.g. in the form of a troche or lozenge. Where appropriate, pharmaceutical compositions for oral administration may be prepared with coatings such as enteric coatings or they can be formulated so as to provide controlled release of the active ingredient such as sustained or prolonged release according to methods well known in the art. Liquid dosage forms for oral administration include e.g. solutions, emulsions, suspensions, syrups and elixirs.

Formulations of the present invention suitable for oral administration may be presented as discrete units such as capsules or tablets, each containing a predetermined amount of the active ingredient, and which may include a suitable excipient. Furthermore, the orally available formulations may be in the form of a powder or granules, a solution or suspension in an aqueous or non-aqueous liquid, or an oil-in-water or water-in-oil liquid emulsion.

Suitable pharmaceutical carriers include inert solid diluents or fillers, sterile aqueous solution and various organic solvents. Examples of solid carriers are lactose, terra alba, sucrose, cyclodextrin, talc, gelatine, agar, pectin, acacia, magnesium stearate, stearic acid, lower alkyl ethers of cellulose, corn starch, potato starch, gums and the like. Examples of liquid carriers are syrup, peanut oil, olive oil, phospholipids, fatty acids, fatty acid amines, polyoxyethylene and water.

The carrier or diluent may include any sustained release material known in the art, such as glyceryl monostearate or glyceryl distearate, alone or mixed with a wax.

Any adjuvants or additives usually used for such purposes such as colourings, flavourings, preservatives etc. may be used provided that they are compatible with the active ingredients.

The amount of solid carrier may vary but will usually be from about 25 mg to about 1 g. If a liquid carrier is used, the preparation may be in the form of a syrup, emulsion, soft gelatine capsule or sterile injectable liquid such as an aqueous or non-aqueous liquid suspension or solution.

Tablets may be prepared by mixing the active ingredient with ordinary adjuvants and/or diluents and subsequently compressing the mixture in a conventional tabletting machine.

Pharmaceutical compositions for parenteral administration include sterile aqueous and nonaqueous injectable solutions, dispersions, suspensions or emulsions as well as sterile powders to be reconstituted in sterile injectable solutions or dispersions prior to use. Depot injectable formulations are also contemplated as being within the scope of the present invention.

For parenteral administration, solutions of the compound of the invention in sterile aqueous solution, aqueous propylene glycol, aqueous vitamin E or sesame or peanut oil may be employed. Such aqueous solutions should be suitably buffered if necessary and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art.

Solutions for injections may be prepared by dissolving the active ingredient and possible additives in a part of the solvent for injection, preferably sterile water, adjusting the solution to the desired volume, sterilising the solution and filling it in suitable ampoules or vials. Any suitable additive conventionally used in the art may be added, such as tonicity agents, preservatives, antioxidants, etc.

Other suitable administration forms include suppositories, sprays, ointments, cremes, gels, inhalants, dermal patches, implants, etc.

A typical oral dosage is in the range of from about 0.001 to about 100 mg/kg body weight per day, preferably from about 0.01 to about 50 mg/kg body weight per day, and more preferred from about 0.05 to about 10 mg/kg body weight per day administered in one or more dosages such as 1, 2 or 3 dosages. The exact dosage will depend upon the frequency and mode of administration, the sex, age, weight and general condition of the subject treated, the nature and severity of the condition treated and any concomitant diseases to be treated and other factors evident to those skilled in the art.

The formulations may conveniently be presented in unit dosage form by methods known to those skilled in the art. A typical unit dosage form for oral administration one or more times per day such as 1, 2 or 3 times per day may contain from 0.01 to about 1000 mg, such as about 0.01 to 100 mg, preferably from about 0.05 to about 500 mg, and more preferred from about 0.5 mg to about 200 mg.

For parenteral routes such as intravenous, intrathecal, intramuscular and similar administration, typically doses are in the order of about half the dose employed for oral administration.

Typical examples of recipes for the formulation of the invention are as follows:

1) Tablets containing 5.0 mg of a compound of the invention calculated as the free base:

| | |
|---|---|
| Compound of the invention | 5.0 mg |
| Lactose | 60 mg |
| Maize starch | 30 mg |
| Hydroxypropylcellulose | 2.4 mg |
| Microcrystalline cellulose | 19.2 mg |
| Croscarmellose Sodium Type A | 2.4 mg |
| Magnesium stearate | 0.84 mg |

2) Tablets containing 0.5 mg of a compound of the invention calculated as the free base:

| | |
|---|---|
| Compound of the invention | 0.5 mg |
| Lactose | 46.9 mg |
| Maize starch | 23.5 mg |
| Povidone | 1.5 mg |

-continued

| | |
|---|---|
| Microcrystalline cellulose | 14.4 mg |
| Croscarmellose Sodium Type A | 1.8 mg |
| Magnesium stearate | 0.63 mg |

3) Syrup containing per milliliter:

| | |
|---|---|
| Compound of the invention | 25 mg |
| Sorbitol | 500 mg |
| Hydroxypropylcellulose | 15 mg |
| Glycerol | 50 mg |
| Methyl-paraben | 1 mg |
| Propyl-paraben | 0.1 mg |
| Ethanol | 0.005 mL |
| Flavour | 0.05 mg |
| Saccharin sodium | 0.5 mg |
| Water | ad 1 mL |

4) Solution for injection containing per milliliter:

| | |
|---|---|
| Compound of the invention | 0.5 mg |
| Sorbitol | 5.1 mg |
| Acetic Acid | 0.05 mg |
| Saccharin sodium | 0.5 mg |
| Water | ad 1 mL |

By the expression a compound of the invention is meant any one of the embodiments of formula IV as described herein.

In a further aspect the present invention relates to a method of preparing a compound of the invention as described in the following.

Methods of Preparation of the Compounds of the Invention

The compounds of the invention may be prepared by conventional synthetic techniques as described in the methods below.

Method 1.

For the preparation of compounds of formula IV with $R^1$=H. Compounds of formula V are deprotected by standard techniques detailed in the textbook *Protective Groups in Organic Synthesis* Greene and Wuts, Wiley Interscience, (1999), ISBN 0471160199. The product of formula IV is isolated as the free base or a salt thereof.

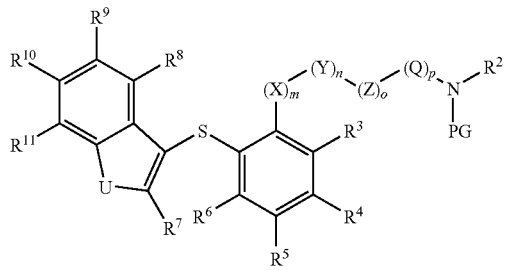

formula V where $R^2$-$R^{11}$, U, X, Y, Z, Q, m, n, o, p are as defined herein and PG is a nitrogen protecting group such as e.g. a tert-butoxycarbonyl group.

Method 2.

For the preparation of compounds of formula IV (for p=1, Q=$CH_2$): Compounds of formula VI are treated with a reducing agent such as e.g. $LiAlH_4$ or $AlH_3$. The product of formula IV is isolated as the free base or a salt thereof.

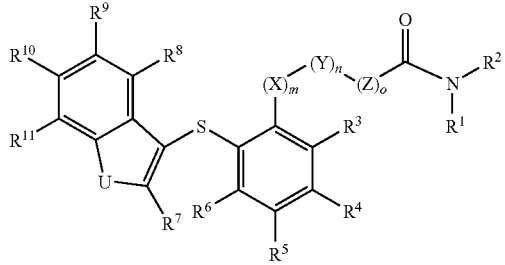

formula VI where $R^1$-$R^{11}$, U, X, Y, Z, m, n, o are as defined herein.

Method 3.

For the preparation of compounds of formula IV (for p=1, Q=$CH_2$): Transformation of the alcohol moiety of a compound of formula VII to a leaving group such as e.g. chloride, bromide, mesylate or tosylate, followed by reaction with an amine of formula VIII in the presence of an appropriate base such as e.g. triethyl amine or excess amine of formula VIII.

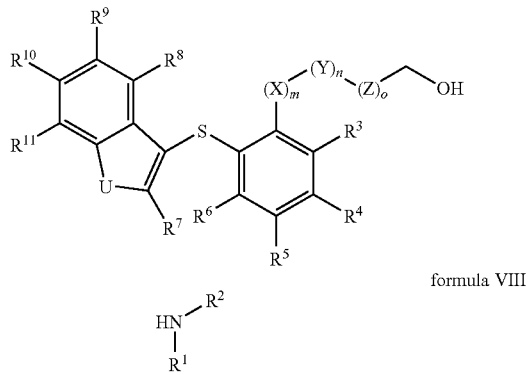

formula VII

formula VIII where $R^1$-$R^{11}$, U, X, Y, Z, m, n, o are as defined herein. Amines of formula VIII are commercially available or can be prepared according to methods described in standard works such as Houben-Weyl, Methoden der organischen Chemie (Methods of Organic Chemistry), Georg-Thieme-Verlag, Stuttgart; Organic Reactions, John Wiley & Sons, Inc. New York, namely under reaction conditions such as those which are known as suitable for such reactions.

Methods of Preparation of Intermediates for the Synthesis of Compounds of the Invention Intermediates for the synthesis of compounds of the invention may be prepared by conventional synthetic techniques as described in the methods below.

Method 4.

For the preparation of compounds of formula V: The appropriate benzo[b]furane or benzo[b]thiophene of formula IX is combined with the appropriate thiol of formula X in the presence of a palladium catalyst and an appropriate base, analogously to methods described in Arnould, J. C. et al. *Tetrahedron Letters*, 1996, 37, 4523 and Winn M. et al. *J Med. Chem.*, 2001, 44, 4393.

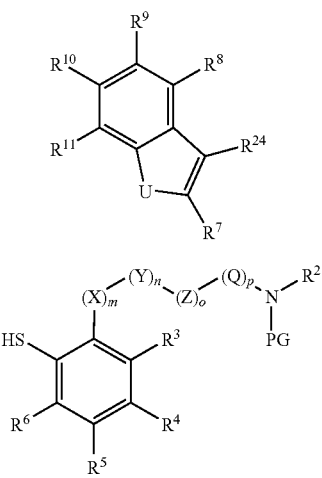

formula IX formula X where $R^2$-$R^{11}$, U, X, Y, Z, Q, m, n, o, p are as defined herein and PG is a nitrogen protecting group such as e.g. a tert-butoxycarbonyl group and $R^{24}$ is a halogen such as iodine or bromine or $R^{24}$ is a pseudo halogen such as e.g. a trifluoro methyl sulphonyl group or a nonafluoro butyl sulphonyl group. Benzo[b]furanes or benzo[b]thiophenes of formula IX are either commercially available or can be prepared according to Method 22.

Method 5.

For the preparation of compounds of formula X: Deprotection of the thiol moiety of a protected thiol of formula XI, by e.g. using a fluoride donor such as e.g. triethylamine tris (hydrogen fluoride).

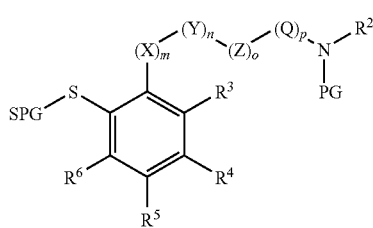

formula XI where $R^2$-$R^6$, X, Y, Z, Q, m, n, o, p are as defined herein, PG is a nitrogen protecting group such as e.g. a tert-butoxycarbonyl group and SPG is a thiol protecting group, e.g. a tri-iso-propyl silyl group.

Method 6.

For the preparation of compounds of formula XI: Reaction of a compound of formula XII with a protected thiol of formula XIII in the presence of a palladium catalyst and an appropriate base, according to Arnould, J. C. et al. *Tetrahedron Letters*, 1996, 37, 4523 and Winn M. et al. *J. Med. Chem.*, 2001, 44, 4393.

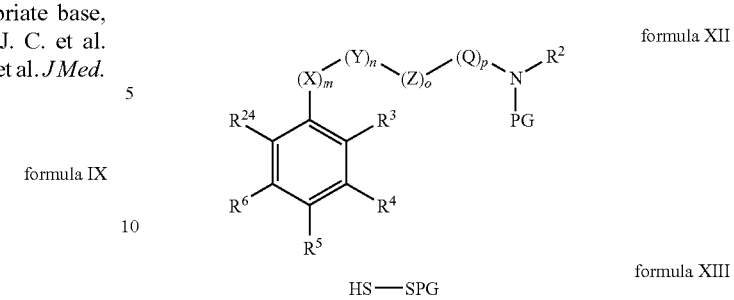

formula XII

HS—SPG formula XIII where $R^2$-$R^6$, X, Y, Z, Q, m, n, o, p are as defined herein, PG is a nitrogen protecting group such as e.g. a tert-butoxycarbonyl group, SPG is a thiol protecting group, e.g. a tri-isopropyl silyl group and $R^{24}$ is a halogen such as iodine or bromine or $R^{24}$ is a pseudo halogen such as e.g. a trifluoro methyl sulphonyl group or a nonafluoro butyl sulphonyl group.

Method 7.

For the preparation of compounds of formula XII (for Q=$CH_2$): Reduction of an amide of formula XIV followed by protection of the nitrogen moiety with a nitrogen protecting group such as e.g. a tert-butoxycarbonyl group.

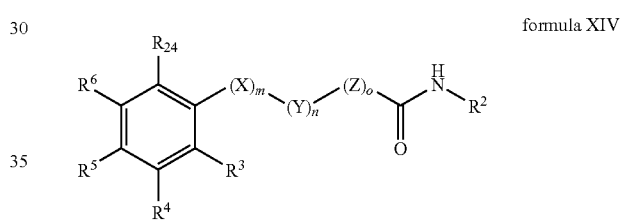

formula XIV where $R^2$-$R^6$, X, Y, Z, m, n, o are as defined herein and $R^{24}$ is a halogen such as iodine or bromine or $R^{24}$ is a pseudo halogen such as e.g. a trifluoro methyl sulphonyl group or a nonafluoro butyl sulphonyl group.

Method 8.

For the preparation of compounds of formula XIV: Activation of a carboxylic acid of formula XV with an activating reagent such as e.g. thionyl chloride or carbonyl diimidazole followed by reaction with an amine of formula XVI.

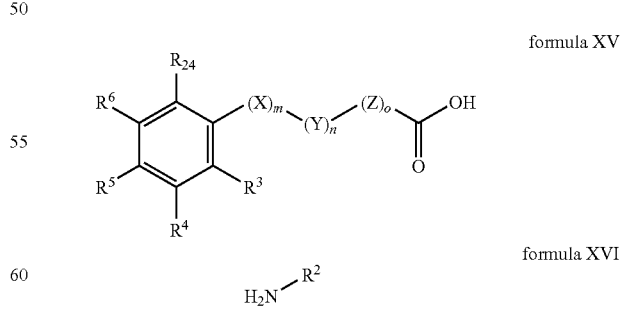

formula XV formula XVI where $R^2$-$R^6$, X, Y, Z, m, n, o are as defined herein and $R^{24}$ is a halogen such as iodine or bromine or $R^{24}$ is a pseudo halogen such as e.g. a trifluoro methyl sulphonyl group or a nonafluoro butyl sulphonyl group. Carboxylic acids of formula XV and amines of formula XVI are commercially available or can be prepared according to methods described in standard works such as Houben-Weyl, Methoden der organischen Chemie (Methods of Organic Chemistry), Georg-Thieme-Verlag, Stuttgart; Organic Reactions, John Wiley & Sons, Inc. New York, namely under reaction conditions such as those which are known as suitable for such reactions.

Method 9.

For the preparation of compounds of formula VI: Activation of a carboxylic acid of formula XVII with an activating reagent such as e.g. carbonyl diimidazole or N,N'-dicyclohexylcarbodiimide followed by reaction with an amine of formula VIII.

formula XVII

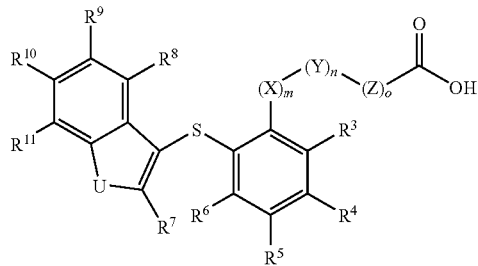

where $R^3$-$R^{11}$, U, X, Y, Z, m, n, o are as defined herein.

Method 10.

For the preparation of compounds of formula XVII: Hydrolysis of a carboxylic acid ester of formula XVIII.

formula XVIII

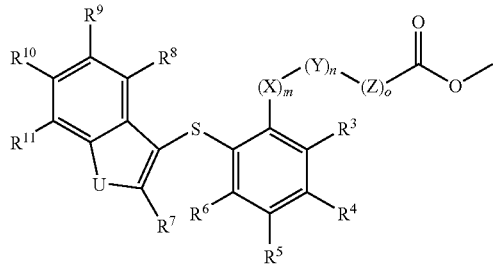

where $R^3$-$R^{11}$, U, X, Y, Z, m, n, o are as defined herein.

Method 11.

For the preparation of compounds of formula VII: Reduction of a carboxylic acid of formula XVII or a carboxylic acid ester of formula XVIII with a reducing agent such as e.g. LiAlH$_4$, AlH$_3$, BH$_3$ or LiBH$_4$.

formula XVII

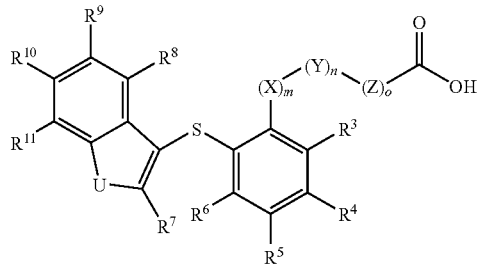

-continued formula XVIII

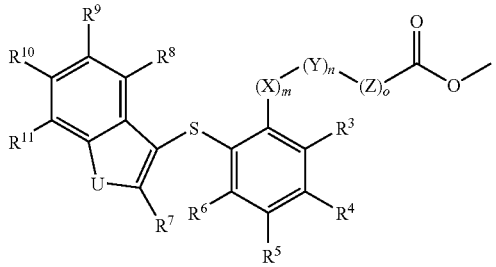

where $R^3$-$R^{11}$, U, X, Y, Z, m, n, o are as defined herein.

Method 12.

For the preparation of compounds of formula XVIII: The appropriate benzo[b]furane or benzo[b]thiophene of formula XIX is combined with the appropriate sulfenyl chloride of formula XX in the presence of a Lewis acid such as e.g. AlCl$_3$, TiCl$_4$ or SiCl$_4$ to generate the desired product of formula XVIII.

formula XIX

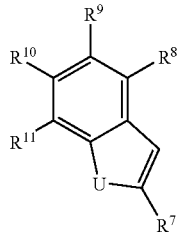

formula XX

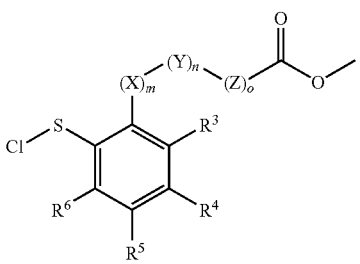

where $R^3$-$R^{11}$, U, X, Y, Z, m, n, o are as defined herein. Benzo[b]furanes or benzo[b]thiophenes of formula XIX are either commercially available or can be prepared according to methods described in standard works such as Houben-Weyl, Methoden der organischen Chemie (Methods of Organic Chemistry), Georg-Thieme-Verlag, Stuttgart; Organic Reactions, John Wiley & Sons, Inc. New York, namely under reaction conditions such as those which are known and suitable for such reactions.

Method 13.

For the preparation of compounds of formula XX: Reaction of a thiophenol of formula XXI with a chlorinating reagent such as N-chloro succinimide.

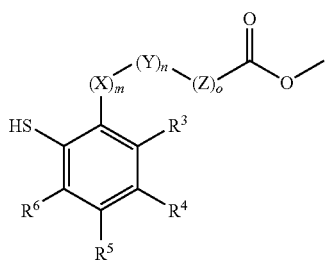

formula XXI where $R^3$-$R^6$, X, Y, Z, m, n, o are as defined herein.

Method 14.

For the preparation of compounds of formula XXI: Deprotection of the thiol moiety of a protected thiol of formula XXII.

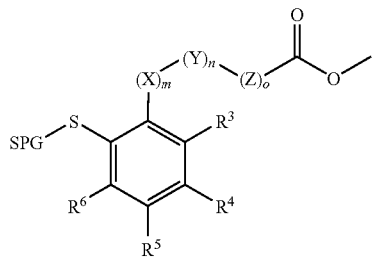

formula XXII where $R^3$-$R^6$, X, Y, Z, m, n, o are as defined herein and SPG is a thiol protecting group, e.g. a tri-iso-propyl silyl group.

Method 15.

For the preparation of compounds of formula XXII: Reaction of a compound of formula XXIII with a protected thiol of formula XIII in the presence of a palladium catalyst and an appropriate base according to Arnould, J. C. et al. *Tetrahedron Letters*, 1996, 37, 4523 and Winn M. et al. *J. Med. Chem.*, 2001, 44, 4393.

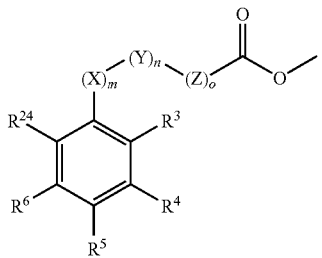

formula XXIII where $R^3$-$R^6$, X, Y, Z, m, n, o are as defined herein and $R^{24}$ is a halogen such as iodine or bromine or $R^{24}$ is a pseudo halogen such as e.g. a trifluoro methyl sulphonyl group or a nonafluoro butyl sulphonyl group.

Method 16.

For the preparation of compounds of formula XXIII: Fischer esterification of a carboxylic acid of formula XV.

Method 17.

For the preparation of compounds of formula XX: Reaction of a disulphide of formula XXIV with a chlorinating reagent such as sulfuryl chloride.

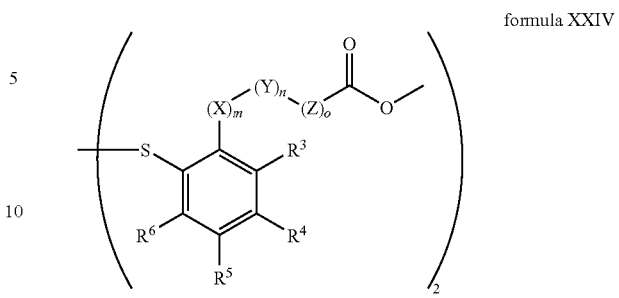

formula XXIV where $R^1$-$R^6$, X, Y, Z, m, n, o are as defined herein.

Method 18.

For the preparation of compounds of formula XXIV: Fischer esterification of a carboxylic acid of formula XXV.

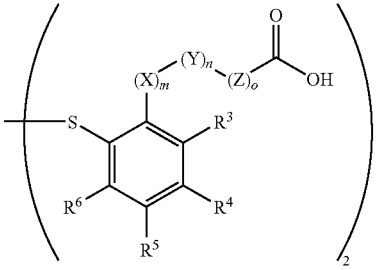

formula XXV where $R^1$-$R^6$, X, Y, Z, m, n, o are as defined herein.

Method 19.

For the preparation of compounds of formula XXV: Reaction of an aniline of formula XXVI with a diazonium salt forming reagent such as e.g. sodium nitrite and subsequent reaction with sodium disulphide as described in Allen C. F. H. et al. *Organic Synthesis*, coll. vol. 2, 580.

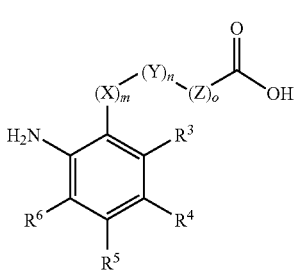

formula XXVI where $R^1$-$R^6$, X, Y, Z, m, n, o are as defined herein. Anilines of formula XXVI are commercially available or can be prepared according to methods described in standard works such as Houben-Weyl, Methoden der organischen Chemie (Methods of Organic Chemistry), Georg-Thieme-Verlag, Stuttgart; Organic Reactions, John Wiley & Sons, Inc. New York, namely under reaction conditions such as those which are known as suitable for such reactions.

Method 20.

For the preparation of compounds of formula XII (for Q=$CH_2$ or $CHR^{21}$): Reductive amination of an aldehyde of formula XXVII or a ketone of formula XXVIII with an amine of formula XVI, using a reducing reagent such as e.g. sodium cyanoborohydride, followed by protection of the nitrogen moiety with a nitrogen protecting group such as e.g. a tert-butoxycarbonyl group.

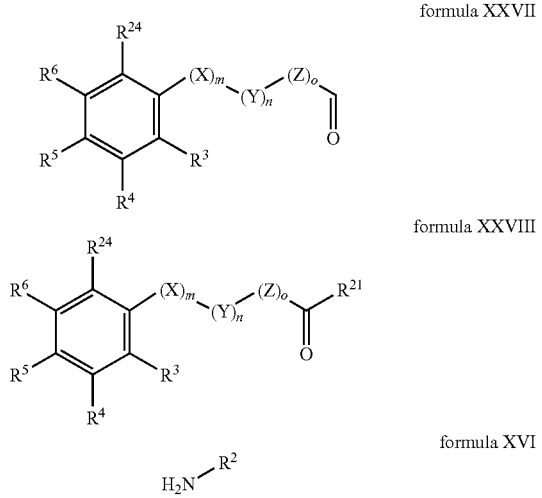

formula XXVII formula XXVIII formula XVI where $R^2$-$R^6$, $R^{21}$, X, Y, Z, m, n, o are as defined herein and $R^{24}$ is a halogen such as iodine or bromine or $R^{24}$ is a pseudo halogen such as e.g. a trifluoro methyl sulphonyl group or a nonafluoro butyl sulphonyl group.

Method 21.

For the preparation of compounds of formula XXVII (for m, n=1, X=CH$_2$, Y=CH$_2$, CHR$^{16}$, R$^{24}$=Br) and for the preparation of compounds of formula XXVIII (for m, n=1, X=CH$_2$, Y=CH$_2$, CHR$^{16}$, R$^{24}$=Br): A tandem Heck—isomerization reaction of a 1-bromo-2-iodobenzene compound of formula XXIX and an olefin of formula XXX or of formula XXXI according to Gibson et al. Synlett 1999, 954 and Qadir et al. Tetrahedron Letters, 44, 2003, 3675.

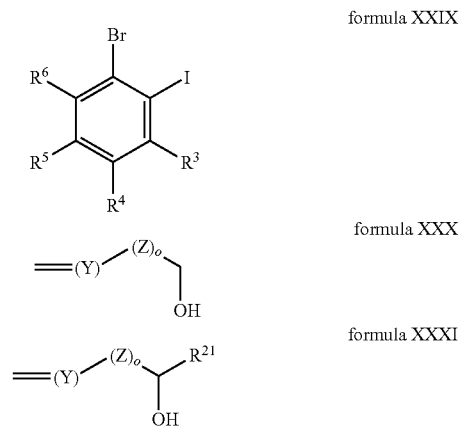

formula XXIX formula XXX formula XXXI where $R^1$-$R^6$, $R^{21}$, Y, Z, o are as defined herein. 1-Bromo-2-iodobenzene compounds of formula XXIX and olefins of formula XXX or of formula XXXI are commercially available or can be prepared according to methods described in standard works such as Houben-Weyl, Methoden der organischen Chemie (Methods of Organic Chemistry), Georg-Thieme-Verlag, Stuttgart; Organic Reactions, John Wiley & Sons, Inc. New York, namely under reaction conditions such as those which are known as suitable for such reactions.

Method 22.

For the preparation of benzo[b]furanes or benzo[b]thiophenes of formula IX (for $R^{24}$=Br):

The appropriate benzo[b]furane or benzo[b]thiophene of formula XIX is brominated with Br$_2$ a to give a compound of formula XXXII, which after treatment with an appropriate base gives 3-bromo-benzo[b]furane or 3-bromo-benzo[b]thiophene of formula IX (with $R^{24}$=Br).

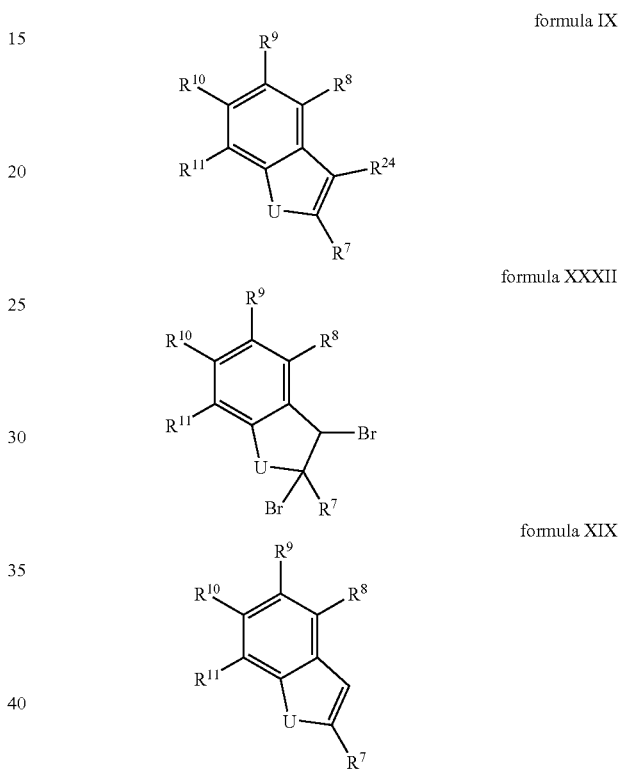

formula IX formula XXXII formula XIX where $R^7$-$R^{11}$, U are as defined herein and $R^{24}$ is Br.

EXAMPLES

Analytical LC-MS data (Method A) were obtained on a PE Sciex API 150EX instrument equipped with atmospheric pressure photo ionisation and a Shimadzu LC-8A/SLC-10A LC system. Column: 30 X 4.6 mm Waters Symmetry C18 column with 3.5 μm particle size; Solventsystem: A=water/trifluoroacetic acid (100:0.05) and B=water/acetonitrile/trifluoroacetic acid (5:95:0.03); Method: Linear gradient elution with 90% A to 100% B in 4 minutes and with a flow rate of 2 mL/minute. Purity was determined by integration of the UV (254 nm) and ELSD trace. The retention times ($t_R$) are expressed in minutes.

Preparative LC-MS-purification was performed on the same instrument with atmospheric pressure chemical ionisation. Column: 50×20 mm YMC ODS-A with 5 μm particle size; Method: Linear gradient elution with 80% A to 100% B in 7 minutes and with a flow rate of 22.7 mL/minute. Fraction collection was performed by split-flow MS detection.

Analytical LC-MS-TOF (TOF=time of flight) data (Method B) were obtained on a micromass LCT 4-ways MUX equipped with a Waters 2488/Sedex 754 detector system. Column: 30×4.6 mm Waters Symmetry C18 column with 3.5 μm particle size; Solventsystem: A=water/trifluoroacetic acid (100:0.05) and B=water/acetonitrile/trifluoroacetic acid (5:95:0.03); Method: Linear gradient elution with 90% A to 100% B in 4 minutes and with a flow rate of 2 mL/minute. Purity was determined by integration of the UV (254 nm) and ELSD trace. The retention times ($t_R$) are expressed in minutes.

The invention disclosed herein is further illustrated by the following non-limiting examples.

Preparation of the Compounds of the Invention

Example 1

Synthesis of 1. [2-(benzo[b]furan-3-ylsulfanyl)-benzyl]-methyl-amine (Method 1)

[2-(Benzo[b]furan-3-ylsulfanyl)-benzyl]-methyl-carbamic acid tert-butyl ester (9.2 g, 24.9 mmol) is dissolved in methanol (75 mL) and diethyl ether saturated with hydrochloric acid (75 mL) is added. The mixture is stirred at ambient temperature for 1 hour and then concentrated in vacuo. Water (50 mL) is added to the remanence and the mixture is basified by addition of aqueous ammonia (conc.). The aqueous fraction is extracted with ethyl acetate (3×100 mL). The combined organic fractions are dried (MgSO$_4$) and concentrated in vacuo. The product is purified by preparative HPLC or by silica gel chromatography eluting with ethyl acetate-triethyl amine (25:1) to furnish the title compound as an oil. This oil can be redissolved in ethyl acetate (75 mL). Diethyl ether saturated with hydrochloric acid can be added hereto until pH 2. The precipitated material can then be filtered off and dried in vacuo to give 6.9 g (91%) of [2-(benzo[b]furan-3-ylsulfanyl)-benzyl]-methyl-amine hydrochloride as a white crystalline material.

Analytical data are shown in Table 2.
The following compounds are prepared analogously:
18. {2-[2-(Benzo[b]thiophen-3-ylsulfanyl)-phenyl]-ethyl}-methyl-amine
19. {2-[2-(Benzo[b]furan-3-ylsulfanyl)-phenyl]-ethyl }-methyl-amine
20. {3-[2-(Benzo[b]thiophen-3-ylsulfanyl)-phenyl]-propyl}-methyl-amine
21. {3-[2-(Benzo[b]furan-3-ylsulfanyl)-phenyl]-propyl}-methyl-amine
22. {4-[2-(Benzo[b]thiophen-3-ylsulfanyl)-phenyl]-butyl }-methyl-amine
23. {4-[2-(Benzo[b]furan-3-ylsulfanyl)-phenyl]-butyl }-methyl-amine Example 2

Synthesis of 9. [2-(benzo[b]thiophen-3-ylsulfanyl)-5-methyl-benzyl]-methyl-amine (Method 2.)

Lithium aluminum hydride (250 g, 6.6 mmol) is suspended in dry diethyl ether (50 mL) and cooled to 0° C. Aluminum chloride (295 mg, 2.2 mmol) dissolved in dry diethyl ether (50 mL) is added dropwise at 0-5° C. The cooling bath is removed and the mixture is stirred at ambient temperature for 1 hour. The resulting aluminum hydride reagent solution is cooled to 0° C. followed by dropwise addition of of 2-(benzo[b]thiophen-3-ylsulfanyl)-5,N-dimethyl-benzamide (327 mg, 2.0 mmol) in 10 mL dry THF. After complete addition the solution is allowed to heat to ambient temperature and stirring is continued for 16 hours. The mixture is cooled to 10° C. followed by slow dropwise addition of water (0.5 mL) followed by 2M sodium hydroxide (0.5 mL) and water (2.5 mL) to quench excessive reducing agent. The mixture is filtered and concentrated in vacuo. The remanence is redissolved in ethyl acetate (100 mL), dried (MgSO$_4$) and concentrated in vacuo. The product is purified by preparative HPLC or by silica gel chromatography eluting with ethyl acetate-triethyl amine to furnish the title compound.

The following compounds are prepared analogously:
10. [2-(Benzo[b]thiophen-3-ylsulfanyl)-4-chloro-benzyl]-methyl-amine
24. 2-(Benzo[b]thiophen-3-ylsulfanyl)-benzylamine Example 3

Synthesis of 3. methyl-[2-(2-methyl-benzo[b]thiophen-3-ylsulfanyl)-benzyl]-amine (Method 3.)

Methanesulfonyl chloride (170 μL, 2.2 mmol) is added to a solution of [2-(2-Methyl-benzo[b]thiophen-3-ylsulfanyl)-phenyl]-methanol (590 mg, 2.1 mmol) and triethyl amine (350 μL, 2.5 mmol) in 10 mL dry THF at 0° C. under an argon atmosphere. The reaction mixture is stirred for 1 hour at room temperature and cooled to 0° C. 2 M methyl amine in THF is added and the reaction is stirred at room temperature for 3 hours. Saturated aqueous NaHCO$_3$ is added and the mixture is extracted with ethyl acetate. The organic phase is washed with brine, dried with MgSO$_4$ and concentrated in vacuo. The residue is purified by flash chromatography on silica gel using ethyl acetate and then ethyl acetate-methanol-triethyl amine (3:1:1) as eluents. This furnishes 460 mg (75%) of the title compound as an oil.

The following compounds were prepared analogously:
2. [2-(Benzo[b]thiophen-3-ylsulfanyl)-benzyl]-methyl-amine
4. [2-(5-Fluoro-benzo[b]thiophen-3-ylsulfanyl)-benzyl]-methyl-amine
5. Methyl-[2-(2-methyl-benzo[b]furan-3-ylsulfanyl)-benzyl]-amine
6. Methyl-[2-(5-methyl-benzo[b]thiophen-3-ylsulfanyl)-benzyl]-amine
7. [2-(5-Chloro-benzo[b]thiophen-3-ylsulfanyl)-benzyl]-methyl-amine Analytical data are shown in Table 2

The following compounds are prepared analogously:
8. [2-(Benzo[b]thiophen-3-ylsulfanyl)-benzyl]-dimethyl-amine
11. [2-(4-Fluoro-benzo[b]thiophen-3-ylsulfanyl)-benzyl]-methyl-amine
12. Dimethyl-[3-(2-methylaminomethyl-phenylsulfanyl)-benzo[b]thiophen-5-yl]-amine
13. Methyl-[2-(7-methyl-benzo[b]thiophen-3-ylsulfanyl)-benzyl]-amine
14. [2-(4,7-Dimethyl-benzo[b]thiophen-3-ylsulfanyl)-benzyl]-methyl-amine
16. Methyl-[2-(6-methyl-benzo[b]thiophen-3-ylsulfanyl)-benzyl]-amine
17. [2-(7-Methoxy-benzo[b]thiophen-3-ylsulfanyl)-benzyl]-methyl-amine
25. 4-[2-(Benzo[b]thiophen-3-ylsulfanyl)-benzyl]-morpholine
26. 4-[2-(Benzo[b]thiophen-3-ylsulfanyl)-benzyl]-thiomorpholine

Preparation of Intermediates

Example 4

Synthesis of [2-(benzo[b]furan-3-ylsulfanyl)-benzyl]-methyl-carbamic acid tert-butyl ester (Method 4., Method 5.)

Methyl-(2-triisopropylsilanylsulfanyl-benzyl)-carbamic acid tert-butyl ester (11.7 g, 28.6 mmol) is dissolved in ethanol (150 mL) and ammonium fluoride (1.10 g, 28.6 mmol) is added. The resulting mixture is stirred at ambient temperature for 30 minutes, then concentrated in vacuo. The remanence is redissolved in dry toluene (175 mL). Tris(dibenzylideneacetone)dipalladium (0) (0.65 g, 0.71 mmol), bis(2-diphenylphosphinophenyl)ether (0.77 g, 1.43 mmol), sodium tert-butoxide (5.50 g, 57.1 mmol) and 3-bromo-benzo[b]furan (5.60g, 28.6 mmol) are added hereto and the resulting mixture is stirred at 100° C. for 1 hour. Upon cooling the mixture is filtered through celite and the filtrate is poured onto a plug of silica. Unpolar byproducts are flushed out with ethyl acetate-heptane (1:20). The product is then eluted with ethyl acetate-heptane (1:9). This furnishes 9.2 g (88%) of the title compound as an oil, which is used in the next step without further purification.

The following intermediates are prepared analogously:
{2-[2-(Benzo[b]thiophen-3-ylsulfanyl)-phenyl]-ethyl}-methyl-carbamic acid tert-butyl ester
{2-[2-(Benzo[b]furan-3-ylsulfanyl)-phenyl]-ethyl}-methyl-carbamic acid tert-butyl ester
{3-[2-(Benzo[b]thiophen-3-ylsulfanyl)-phenyl]-propyl}-methyl-carbamic acid tert-butyl ester
{3-[2-(Benzo[b]furan-3-ylsulfanyl)-phenyl]-propyl}-methyl-carbamic acid tert-butyl ester
{4-[2-(Benzo[b]thiophen-3-ylsulfanyl)-phenyl]-butyl}-methyl-carbamic acid tert-butyl ester
{4-[2-(Benzo[b]furan-3-ylsulfanyl)-phenyl]-butyl}-methyl-carbamic acid tert-butyl ester

Example 5

Synthesis of methyl-(2-triisopropylsilanylsulfanyl-benzyl)-carbamic acid tert-butyl ester (Method 6.)

(2-Iodo-benzyl)-methyl-carbamic acid tert-butyl ester (3.0 g, 8.64 mmol), tris(dibenzylideneacetone)dipalladium (0) (79 mg, 0.086 mmol), bis(2-diphenylphosphinophenyl)ether (93 mg, 0.17 mmol), sodium tert-butoxide (1.10 g, 11.2 mmol), triisopropylsilanethiol (1.73 g, 9.07 mmol) and dry toluene (15 mL) are all placed in an Emrys Optimizer EXP 20 mL microwave reactor tube. The reaction vessel is sealed and subjected to microwave heating at 160° C. for 15 minutes. Upon cooling the mixture is poured onto a plug of silica and the product is eluted with ethyl acetate-heptane (1:4). This procedure is repeated an additional 3 times to furnish a total of 13.7 g (97%) of the title compound as an oil which is used in the next step without further purification.

The following compounds were prepared analogously:
Methyl-[2-(2-triisopropylsilanylsulfanyl-phenyl)-ethyl]-carbamic acid tert-butyl ester
Methyl-[3-(2-triisopropylsilanylsulfanyl-phenyl)-propyl]-carbamic acid tert-butyl ester
Methyl-[4-(2-triisopropylsilanylsulfanyl-phenyl)-butyl]-carbamic acid tert-butyl ester

Example 6

Synthesis of (2-iodo-benzyl)-methyl-carbamic acid tert-butyl ester (Method 7.)

Lithium aluminum hydride (14.8 g, 390 mmol) is suspended in dry diethyl ether (250 mL) and cooled to 0° C. Aluminum chloride (16.0 g, 121 mmol) dissolved in dry diethyl ether (250 mL) is added dropwise at 0-5° C. The cooling bath is removed and the mixture is stirred at ambient temperature for 1 hour. The resulting aluminum hydride reagent solution is cooled to 0° C. followed by dropwise addition of 2-iodo-N-methyl-benzamide (50.8 g, 195 mmol) dissolved in dry THF (500 mL). After complete addition the solution is allowed to heat to ambient temperature and stirring is continued for 16 hours. The mixture is cooled to 10° C. followed by slow dropwise addition of water (30 mL) followed by 2M sodium hydroxide (30 mL) and water (150 mL). $MgSO_4$ is added and the mixture is stirred for 10 minutes, filtered and concentrated in vacuo. The remanence is redissolved in ethyl acetate (500 mL), dried ($MgSO_4$) and concentrated again to furnish 45.2 g (94%) of (2-iodo-benzyl)-methyl-amine as an oil. (2-Iodo-benzyl)-methyl-amine (20.0 g, 80.9 mmol) is dissolved in dry THF (300 mL) and di-tert-butyl dicarbonate (18.5 g, 85.0 mmol) is added. The mixture is stirred for 1 hour at ambient temperature. The volatiles are removed by means of evaporation and the crude mixture is purified by silica gel chromatography eluting with ethyl acetate-heptane (1:4) to furnish 28.5 g (quant.) of the title compound as an oil.

The following intermediates were prepared analogously:
[2-(2-Iodo-phenyl)-ethyl]-methyl-carbamic acid tert-butyl ester
[4-(2-Bromo-phenyl)-butyl]-methyl-carbamic acid tert-butyl ester

Example 7

Synthesis of 2-iodo-N-methyl-benzamide (Method 8)

Thionyl chloride (29.4 mL, 404 mmol) is added to a solution of (2-iodo-benzoic acid (50.0 g, 202 mmol) in dry toluene (600 mL). The mixture is heated to reflux for 4 hours and the solvent is removed in vacuo. The remanence is redissolved in dry toluene (600 mL) and cooled to 0° C. 40% methylamine (aq., 94.1 mL, 1.21 mol) is added dropwise at 0-5° C. during 30 minutes. The mixture is then stirred at ambient temperature for 16 hours, poured onto water (300 mL) and extracted with ethyl acetate (3×300 mL) The combined organic fractions are washed successively with saturated sodium bicarbonate solution (250 mL) and brine (250 mL), dried ($MgSO_4$) and concentrated in vacuo. This gives 50.8 g (96%) of crystalline 2-iodo-N-methyl-benzamide.

The following intermediates were prepared analogously:
2-(2-Iodo-phenyl)-N-methyl-acetamide
4-(2-Bromo-phenyl)-N-methyl-butyramide

Example 8

Synthesis of [3-(2-bromo-phenyl)-propyl]-methyl-carbamic acid tert-butyl ester (Method 20.)

Methyl amine (8M in ethanol, 38 mL, 304 mmol) is added to 3-(2-bromo-phenyl)-propionaldehyde (6.32 g, 29.7 mmol) and sodium cyanoborohydride (2.24 g, 35.6 mmol) in methanol. The reaction mixture is cooled to 0° C. and acetic acid is added slowly until pH<7. The reaction mixture is stirred for ½ hour and neutralized with aqueous sodium hydroxide. Methanol is removed in vacuo and ethyl acetate and brine are added. The aqueous phase is extracted with ethyl acetate and the combined organic phases are dried with MgSO$_4$ and concentrated in vacuo. The residue is dissolved in THF (150 mL) and di-tert-butyl dicarbonate (7.2 g, 33 mmol) and triethyl amine (5.2 mL, 37.1 mmol) are added. The reaction mixture is stirred for 2 hours, filtered through silica gel and concentrated in vacuo. The residue is purified by flash chromatography (silica gel, ethyl acetate/heptane) to give 3.23 g (33%) of the title compound.

Example 9

Synthesis of 3-bromo-benzo[b]furan (Method 22.)

Bromine (13.1 mL, 250 mmol) dissolved in chloroform (50 mL) is added dropwise to a solution of benzo[b]furan (25 g, 210 mmol) in chloroform (200 mL) at −10° C. over 20 minutes. The mixture is then stirred at 0° C. for 1 hour and the volatiles are evaporated. The residue is stirred with ethanol (50 mL) and then filtered. The solid material is washed with diethyl ether (100 mL) on the filter. This furnishes 23.0 g (39%) of 2,3-dibromo-2,3-dihydro-benzo[b]furan as white crystalline material. Potassium hydroxide pellets (9.3 g, 165 mmol) are dissolved in ethanol (40 mL) and cooled to 0° C. 2,3-Dibromo-2,3-dihydro-benzo[b]furan (23.0 g, 82.7 mmol) dissolved in ethanol (90 mL) is added dropwise hereto at a constant temperature of 0° C. After complete addition the mixture is heated to reflux for 2 hours. The mixture is concentrated in vacuo and water (100 mL) is added. The aqueous layer is extracted with ethyl acetate (3×100 mL). The combined organic fractions are washed with brine (100 mL), dried (MgSO$_4$) and concentrated to furnish 14.7g (90%) of the wanted product as an oil.

Example 10

Synthesis of [2-(2-methyl-benzo[b]thiophen-3-ylsulfanyl)-phenyl]-methanol (Method 11.)

Lithium aluminum hydride (250 mg, 6.6 mmol) is added to a solution of 2-(2-methyl-benzo[b]thiophen-3-ylsulfanyl)-benzoic acid methyl ester (651 mg, 2.07 mmol) in 10 mL dry THF at 0° C. The reaction mixture is stirred for 16 hours at room temperature. The reaction is quenched with 0.5 mL water. The reaction mixture is stirred for ½ hour and 0.25 mL 15% NaOH (aq) is added. The reaction mixture is stirred for 1 hour, then 1 mL water is added and stirring is continued for another hour. The mixture is filtered, dried with MgSO$_4$ and concentrated in vacuo to give the title compound, which is used without further purification.

The following intermediates were prepared analogously:
[2-(Benzo[b]thiophen-3-ylsulfanyl)-phenyl]-methanol
[2-(5-Fluoro-benzo[b]thiophen-3-ylsulfanyl)-phenyl]-methanol
[2-(2-Methyl-benzo[b]furan-3-ylsulfanyl)-phenyl]-methanol
[2-(5-Methyl-benzo[b]thiophen-3-ylsulfanyl)-phenyl]-methanol
[2-(5-Chloro-benzo[b]thiophen-3-ylsulfanyl)-phenyl]-methanol
3-(2-Bromo-phenyl)-propan-1-ol The following intermediates are prepared analogously:
[2-(4-Fluoro-benzo[b]thiophen-3-ylsulfanyl)-phenyl]-methanol
[2-(5-Dimethylamino-benzo[b]thiophen-3-ylsulfanyl)-phenyl]-methanol
[2-(7-Methyl-benzo[b]thiophen-3-ylsulfanyl)-phenyl]-methanol
[2-(4,7-Dimethyl-benzo[b]thiophen-3-ylsulfanyl)-phenyl]-methanol
[2-(6-Methyl-benzo[b]thiophen-3-ylsulfanyl)-phenyl]-methanol
[2-(7-Methoxy-benzo[b]thiophen-3-ylsulfanyl)-phenyl]-methanol Example 11

Synthesis of 2-(methoxycarbonyl)phenyl sulfenyl chloride (Method 17.)

Sulfuryl chloride (0.88 mL, 11 mmol) is added to methyl 2-[[2-(methoxycarbonyl)phenyl]dithio]benzoate in 75 ml dry 1,2-dichloro-ethane. The reaction mixture is stirred for 1 hour at room temperature to give a 0.29 M solution of 2-(methoxycarbonyl)phenyl sulfenyl chloride.

Example 12

Synthesis of 2-(2-methyl-benzo[b]thiophen-3-ylsulfanyl)-benzoic acid methyl ester (Method 12.)

2-(Methoxycarbonyl)phenyl sulfenyl chloride (10 mL 0.29 M solution in 1,2-dichloro-ethane, 2.9 mmol) is added to a solution of 2-methyl-benzo[b]thiophene (445 mg, 3mmol) in 5 mL 1,2-dichloro-ethane. The reaction mixture is cooled to 0° C. Aluminium chloride (400 mg, 3 mmol) is added and the reaction mixture is stirred for 4 hours at room temperature. The reaction is quenched with water. The organic phase is washed with brine, dried with MgSO$_4$ and concentrated in vacuo. The residue is purified by flash chromatography on silica gel using ethyl acetate-heptane as eluent. This furnishes 651 mg (69%) of the title compound as an oil.

The following intermediates were prepared analogously:
2-(Benzo[b]thiophen-3-ylsulfanyl)-benzoic acid methyl ester
2-(5-Fluoro-benzo[b]thiophen-3-ylsulfanyl)-benzoic acid methyl ester
2-(2-Methyl-benzo[b]furan-3-ylsulfanyl)-benzoic acid methyl ester
2-(5-Methyl-benzo[b]thiophen-3-ylsulfanyl)-benzoic acid methyl ester
2-(5-Chloro-benzo[b]thiophen-3-ylsulfanyl)-benzoic acid methyl ester The following intermediates are prepared analogously:
2-(4-Fluoro-benzo[b]thiophen-3-ylsulfanyl)-benzoic acid methyl ester
2-(5-Dimethylamino-benzo[b]thiophen-3-ylsulfanyl)-benzoic acid methyl ester
2-(7-Methyl-benzo[b]thiophen-3-ylsulfanyl)-benzoic acid methyl ester
2-(4,7-Dimethyl-benzo[b]thiophen-3-ylsulfanyl)-benzoic acid methyl ester
2-(6-Methyl-benzo[b]thiophen-3-ylsulfanyl)-benzoic acid methyl ester
2-(7-Methoxy-benzo[b]thiophen-3-ylsulfanyl)-benzoic acid methyl ester
2-(Benzo[b]thiophen-3-ylsulfanyl)-5-methyl-benzoic acid methyl ester 2-(Benzo[b]thiophen-3-ylsulfanyl)-4-chloro-benzoic acid methyl ester Example 13

Synthesis of methyl 2-[[2-(methoxycarbonyl)phenyl]dithio]benzoate (Method 18.)

6 mL Sulphuric acid is added to '2,2'-dithiodibenzoic acid (20 g, 65.3 mmol) in 150 mL methanol. The reaction mixture is refluxed 3 days. The reaction mixture is cooled to room temperature and saturated aqueous $NaHCO_3$ is added. Methanol is removed in vacuo. The resulting heterogeneous mixture is extracted with ethyl acetate. The organic phase is washed with brine, dried with $MgSO_4$ and concentrated in vacuo to give 17.8 g (82%) of the title compound as a solid, which is used without further purification.

Example 14

Synthesis of 2-methoxycarbonyl-4-methyl-benzenesulfenyl chloride (Method 13, Method 14.)

Triethylamine tris(hydrogen fluoride) (500 μL, 3.1 mmol) is added to (2-triisopropylsilanylsulfanyl-phenyl)-acetic acid methyl ester in THF (10 mL) The resulting mixture is stirred at 50° C. for 30 minutes, then concentrated in vacuo. The residue is put on a silica gel plug and (2-mercapto-phenyl)-acetic acid methyl ester is eluted with ethyl acetate-heptane (1:4) and concentrated in vacuo.

The following intermediate is prepared analogously:
4-Chloro-2-mercapto-benzoic acid methyl ester
2-Mercapto-5-methyl-benzoic acid methyl ester (from above) is dissolved in 15 mL 1,2-dichloro-ethane and added to N-chloro succinimide (414 mg, 3.1 mmol) in 10 mL 1,2-dichloro-ethane at 0° C. The resulting mixture is stirred at room temperature for 15 minutes to give a solution of the title compound, which is used without purification.

The following intermediate is prepared analogously:
3-chloro-6-methoxycarbonyl-benzenesulfenyl chloride Example 15

Synthesis of 5-methyl-2-triisopropylsilanylsulfanyl-benzoic acid methyl ester (Method 15.)

2-Bromo-5-methyl-benzoic acid methyl ester (2.06 g, 9.00 mmol), tris(dibenzylideneacetone)dipalladium (0) (83 mg, 0.09 mmol), bis(2-diphenylphosphinophenyl)ether (97 mg, 0.18 mmol), sodium tert-butoxide (1.00 g, 10.4 mmol), tri-isopropylsilanethiol (1.37g, 7.2 mmol) and dry toluene (10 mL) are all placed in an Emrys Optimizer EXP 20 mL microwave reactor tube. The reaction vessel is sealed and subjected to microwave heating at 150° C. for 30 minutes. Upon cooling the mixture is poured onto a plug of silica and the product is eluted with ethyl acetate-heptane (2:8). This furnishes the title compound as an oil, which is used in the next step without further purification.

The following intermediate is prepared analogously:
4-Chloro-2-triisopropylsilanylsulfanyl-benzoic acid methyl ester Example 16

Synthesis of 2-bromo-5-methyl-benzoic acid methyl ester (Method 16.)

1 mL $H_2SO_4$ is added to 2-bromo-5-methyl-benzoic acid (7.5 g, 70 mmol) in 75 mL methanol. The reaction mixture is refluxed 16 hours and cooled to room temperature. 100 mL saturated $NaHCO_3$ (aq) is added. Methanol is removed in vacuo. The resulting mixture is extracted with ethyl acetate. The organic phase is washed with brine, dried with $MgSO_4$ and concentrated in vacuo to give the title compound.

The following intermediates are prepared analogously:
2-Bromo-4-chloro-benzoic acid methyl ester
Methyl 2-[[2-(methoxycarbonyl)phenyl]dithio]benzoate Example 17

Synthesis of 2-(Benzo[b]thiophen-3-ylsulfanyl)-5,N-dimethyl-benzamide (Method 9.)

Carbonyldiimidazole (324 mg, 2 mmol) is added to 2-(benzo[b]thiophen-3-ylsulfanyl)-5-methyl-benzoic acid (300 mg, 1 mmol) in mL dry THF and stirred for 2 hours at room temperature. 2.5 mL methyl amine (2M in THF, 5 mmol) is added and the reaction mixture is stirred for 16 hours at room temperature. Ethyl acetate is added and the organic phase is washed with 1 N HCl (aq) and brine, dried with $MgSO_4$ and concentrated in vacuo to give the title compound, which is used in the next step without further purification.

The following intermediates are prepared analogously:
2-(Benzo[b]thiophen-3-ylsulfanyl)-4-chloro-N-methyl-benzamide
2-(Benzo[b]thiophen-3-ylsulfanyl)-benzamide Example 18

Synthesis of 2-(benzo[b]thiophen-3-ylsulfanyl)-5-methyl-benzoic acid (Method 10.)

LiOH (480 mg, 20 mmol) is added to 2-(benzo[b]thiophen-3-ylsulfanyl)-5-methyl-benzoic acid methyl ester (630 mg, 2 mmol) in 16 mL mixture of THF/water (3:1). The reaction mixture is refluxed for 2 hours and cooled to room temperature. Water and ethyl acetate is added and the organic phase is washed with brine, dried with $MgSO_4$ and concentrated in vacuo to give the title compound, which is used in the next step without further purification.

The following intermediates are prepared analogously:
2-(Benzo[b]thiophen-3-ylsulfanyl)-4-chloro-benzoic acid
2-(Benzo[b]thiophen-3-ylsulfanyl)-benzoic acid Example 19

Synthesis of 4-(2-bromo-phenyl)-butyric acid

Methanesulfonyl chloride (7.7 mL, 97 mmol) in 100 mL dry THF is added to a solution of 3-(2-bromo-phenyl)-propan-1-ol (17.4 g, 80.9 mmol) and triethyl amine (14.7 g, 146 mmol) in 200 mL dry THF at 0° C. under an argon atmosphere. Water is added and the mixture is extracted with ethyl acetate. The organic phase is washed with brine, dried with $MgSO_4$ and concentrated in vacuo to give 23 g (97%) methanesulfonic acid 3-(2-bromo-phenyl)-propyl ester as an oil. Methanesulfonic acid 3-(2-bromo-phenyl)-propyl ester (23g, 78 mmol) in 300 mL dry DMF is added to a suspension of potassium cyanide (15.3 g, 235 mmol) in dry DMF. The reaction mixture is stirred at 60° C. for 16 hours. Water is added and the mixture is extracted with ethyl acetate (3 times). The organic phase is washed with brine (twice), dried with MgSO$_4$ and concentrated in vacuo. The residue is placed on a plug of silica gel and eluted with ethyl acetate/heptane (1:4) and concentrated in vacuo to give 16.0 g 4-(2-bromo-phenyl)-butyronitrile (91%) as an oil. 300 mL concentrated HCl is added to 4-(2-bromo-phenyl)-butyronitrile (16.0 g, 71 mmol) in 150 mL acetic acid. The reaction mixture is stirred at 60° C. for 16 hours. The reaction mixture concentrated in vacuo partly and is poured into water. The mixture is extracted with ethyl acetate (3 times). The organic phase is washed with brine (twice), dried with MgSO$_4$ and concentrated in vacuo to give the title compound as a crystalline material.

TABLE 2

Measured molecular mass (M + H$^+$), measured HPLC-retention time ($t_R$, min) and UV- and ELSD-purities (%).

| Compound | LC/MS method | $t_R$ min. | UV-purity (%) | ELSD-purity (%) | M + H$^+$ |
|---|---|---|---|---|---|
| 1 | A | 1.79 | 97 | 100 | 269.9 |
| 2 | A | 1.9 | 100 | 100 | 285.9 |
| 3 | A | 2.05 | 99 | 99 | 300.1 |
| 4 | A | 1.94 | 98 | 99 | 304.0 |
| 5 | A | 1.95 | 98 | 99 | 284.1 |
| 6 | A | 2.05 | 82 | 100 | 299.9 |
| 7 | A | 2.07 | 93 | 99 | 319.9 |

TABLE 1

Reagents used for the preparation of compounds in Examples 1-19.

| Name | Supplier | CAS no. | Cat. no. |
|---|---|---|---|
| Benzo[b]furan | Aldrich | 271-89-6 | B800-2 |
| 2-Methylbenzo[b]furan | Aldrich | 4265-25-2 | 22,434-0 |
| Benzo[b]thiophene | | 95-15-8 | |
| 3-Bromobenzo[b]thiophene | Aldrich | 7342-82-7 | 49,497-6 |
| 2-Methylbenzo[b]thiophene | Aldrich | 1195-14-8 | 46,745-6 |
| 5-Methylbenzo[b]thiophene | ABCR | 14315-14-1 | AV12666 |
| 2,5-Dimethylthiophenol | Aldrich | 4001-61-0 | 27,546-8 |
| 4-Fluorothiophenol | Aldrich | 371-42-6 | F1,531-5 |
| 4-Chlorothiophenol | ALFA-DM | 106-54-7 | 19445 |
| 1-Bromo-4-fluoro-2-iodobenzene | Aldrich | 202865-72-3 | 52,893-5 |
| 4-(Dimethylamino)thiophenol | Oakwood | 494622-9 | 23125 |
| 2-Thiocresol | Aldrich | 137-06-4 | T2,850-9 |
| 4-Hydroxythiophenol | Aldrich | 637-89-8 | 27,539-5 |
| 2-Methoxybenzenethiol | Aldrich | 7217-59-6 | 18,405-5 |
| 2-Bromo-3-methylaniline | Aldrich | 54879-20-8 | 64,562-1 |
| Bromoacetaldehyde diethyl acetal | Aldrich | 2032-35-1 | 12,398-6 |
| Bromoacetaldehyde diethyl acetal | Aldrich | 7252-83-7 | 24,250-0 |
| Polyphosphoric acid | Aldrich | 8017-16-1 | F20,821-3 |
| Methylamine | Aldrich | 74-89-5 | 42,646-6 |
| Dimethylamine | Aldrich | 124-40-3 | 39,195-6 |
| Morpholine | Aldrich | 110-91-8 | 25,236-0 |
| Thiomorpholine | Fluka | 123-90-0 | 88885 |
| 2,2'-Dithiodibenzoic acid | Fluka | 119-80-2 | 43761 |
| 2-Iodobenzoic acid | Aldrich | 88-67-5 | I7675 |
| 2-Iodo-5-methylbenzoic acid | Transwld | 52548-14-8 | I1188-B |
| 2-Bromo-4-chlorobenzoic acid | Matrix | 936-08-3 | 1635 |
| 2-Iodophenylacetic acid | Aldrich | 18698-96-9 | 53,147-2 |
| 3-(2-Bromophenyl)propionic acid | Transwld | 15115-58-9 | B3193 |
| 1-Bromo-2-iodobenzene | Aldrich | 583-55-1 | 24,261-6 |
| Allyl alcohol | Aldrich | 107-18-6 | 24,053-2 |
| Di-tert-butyl dicarbonate | Fluka | 24424-99-5 | 34660 |
| 3-Buten-1-ol | Aldrich | 627-27-0 | 11,036-1 |
| N-Chlorosuccinimide | Aldrich | 128-09-6 | 10,968-1 |
| Bromine | Aldrich | 7726-95-6 | 40,718-6 |
| Sulfuryl Chloride | Aldrich | 7791-25-5 | 27,850-5 |
| Methanesulfonyl chloride | Aldrich | 124-63-0 | 47,125-9 |
| Triisopropylsilanethiol | Aldrich | 156275-96-6 | 42,993-7 |
| Bis(2-diphenylphosphinophenyl)ether | Aldrich | 166330-10-5 | 51,001-7 |
| Tris(dibenzylideneacetone)dipalladium (0) | Aldrich | 52409-22-0 | 32,877-4 |
| Sodium tert-butoxide | Aldrich | 865-48-5 | 35,927-0 |
| Ammonium fluoride | Fluka | 12125-01-8 | 09737 |
| Triethylamine tris(hydrogen fluoride) | Aldrich | 73602-61-6 | 34,464-8 |
| Sodium cyanoborohydride | Aldrich | 25895-60-7 | 15,615-9 |
| Lithium aluminum hydride | Aldrich | 16853-85-3 | 21,277-6 |
| Aluminum chloride | Aldrich | 7446-70-0 | 29,471-3 |
| 1,1'-Carbonyldiimidazole | Aldrich | 530-62-1 | 11,553-3 |
| N,N'-Dicyclohexylcarbodiimide | Aldrich | 538-75-0 | D8,000-2 |
| Thionyl chloride | Acros | 7719-09-7 | 16949-0010 |

NA: not available

Example 20

Transporter Inhibition Assay

Measurements of [$^3$H]-5-HT Uptake into Rat Cortical Synaptosomes

Whole brains from male Wistar rats (125-225 g), excluding cerebellum, are homogenized in 0.40 M sucrose supplemented with 1 mM nialamid with a glass/teflon homogenizer. The homogenate is centrifuged at 1000×g for 10 min at 4 °C. The pellet is discarded and the supernatant is centrifuged at 40.000×g for 20 min. The final pellet is homogenized in assay buffer (0.5 mg original tissue/well). Test compounds (or buffer) and 10 nM [$^3$H]-5-HT are added to 96 well plates. Composition of assay buffer: 123 mM NaCl, 4.82 mM KCl, 0.973 mM $CaCl_2$, 1.12 mM $MgSO_4$, 12.66 mM $Na_2HPO_4$, 2.97 mM $NaH_2PO_4$, 0.162 mM EDTA, 2 g/l glucose and 0.2 g/l ascorbic acid. Buffer is oxygenated with 95% $O_2$/5% $CO_2$ for 10 min. The incubation is started by adding tissue to a final assay volume of 0.2 mL. After 15 min incubation with radioligand at 37° C., samples are filtered directly on Unifilter GF/C glass fiber filters (soaked for 30 min in 0.1% polyethylenimine) under vacuum and immediately washed with 1×0.2 ml assay buffer. Non-specific uptake is determined using citalopram (10 μM final concentration). Citalopram is included as reference in all experiments as dose-response curve.

Measurements of [$^3$H]noradrenaline Uptake into Rat Cortical Synaptosomes

Fresh occipital-, temporal- and parietal cortex from male Wistar rats (125-225 g) are homogenized in 0.4 M sucrose with a glass/teflon homogenizer. The homogenate is centrifuged at 1000×g for 10 min at 4° C. The pellet is discarded and the supernatant is centrifuged at 40.000×g for 20 min. The final pellet is homogenized in this assay buffer: 123 mM NaCl, 4.82 mM KCl, 0.973 mM $CaCl_2$, 1.12 mM $MgSO_4$, 12.66 mM $Na_2HPO_4$, 2.97 mM $NaH_2PO_4$, 0.162 mM EDTA, 2 g/l glucose and 0.2 g/l ascorbic acid (7.2 mg original tissue/mL=1 mg/140 μl). Buffer is oxygenated with 95% $O_2$/5% $CO_2$ for 10 min. Pellet is suspended in 140 volumes of assay buffer. Tissue is mixed with test compounds and after 10 min pre-incubation, 10 nM [$^3$H]-noradrenaline is added to a final volume of 0.2 ml and the mixture is incubated for 15 min at 37° C. After 15 min incubation, samples are filtered directly on Unifilter GF/C glass fiber filters (soaked for 30 min in 0.1% polyethylenimine) under vacuum and immediately washed with 1×0.2 mL assay buffer. Non-specific uptake is determined using talsupram (10 μM final concentration). Duloxetine is included as reference in all experiments as dose-response curve.

Measurements of [$^3$H]dopamine Uptake into Rat Cortical Synaptosomes

Tissue preparation: male wistar rats (125-250 g) are sacrificed by decapitation and striatum quickly dissected out and placed in ice cold 0.40 M sucrose. The tissue is gently homogenised (glass teflon homogeniser) and the P2 fraction is obtained by centrifugation (1000 g, 10 minutes and 40000 g, 20 minutes, 4° C.) and suspended in 560 volumes of a modified Krebs-Ringer-phosphate buffer, pH 7.4.

Tissue 0.25 mg/well(140 μl) (original tissue) is mixed with test suspension. After 5 minutes pre-incubation at room temperature, 12.5 nM 3H-dopamine is added and the mixture is incubated for 5 minutes at room temperature. Final volume is 0.2 mL.

The incubation is terminated by filtering the samples under vacuum through Whatman GF/C filters with a wash of 1×0.2 ml buffer. The filters are dried and appropriate scintillation fluid (Optiphase Supermix) is added. After storage for 2 hours in the dark the content of radioactivity is determined by liquid scintillation counting. Uptake is obtained by subtracting the non-specific binding and passive transport measured in the presence of 100 μM of benztropin. For determination of the inhibition of uptake ten concentrations of drugs covering 6 decades are used.

$^3$H-DA=3.4-(ring-2,5,6-$^3$H)dopamine hydrochloride from New England Nuclear, specific activity 30-50 Ci/mmol.

Hyttel, Biochem. Pharmacol. 1978, 27, 1063-1068;

Hyttel, Prog. Neuro-Psychopharmacol. & bil. Psychiat. 1982, 6, 277-295;

Hyttel & Larsen, Acta Pharmacol. Tox. 1985, 56, suppl. 1, 146-153.

The invention claimed is:

1. A compound of the general formula IV:

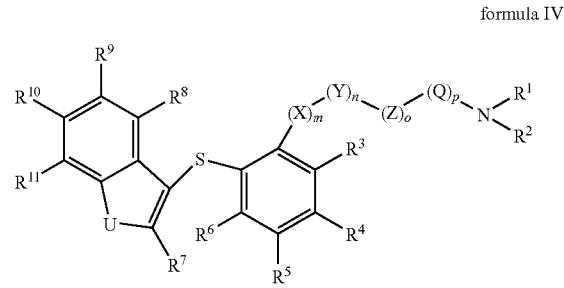

formula IV wherein;

U is sulphur;

$R^1$-$R^2$ are independently selected from the group consisting of hydrogen, $C_{1-6}$-alk(en/yn)yl, $C_{3-8}$-cycloalk(en)yl, and $C_{3-8}$-cycloalk(en)yl-$C_{1-6}$-alk(en/yn)yl; or $R^1$ and $R^2$ together with the nitrogen to which they are attached form a 4-7 membered ring containing zero or one double bond, optionally said ring in addition to said nitrogen comprises one further heteroatom selected from oxygen and sulphur;

$R^3$-$R^6$ are independently selected from the group consisting of hydrogen, halogen, cyano, $C_{1-6}$-alk(en/yn)yl, $C_{3-8}$-cycloalk(en)yl, $C_{3-8}$-cycloalk(en)yl-$C_{1-6}$-alk(en/yn)yl, halo-$C_{1-6}$-alk(en/yn)yl, halo-$C_{3-8}$-cycloalk(en)yl and halo-$C_{3-8}$-cycloalk(en)yl-$C_{1-6}$-alk(en/yn)yl;

$R^7$ is selected from the group consisting of hydrogen, $C_{1-6}$-alk(en/yn)yl, $C_{3-8}$-cycloalk(en)yl and $C_{3-8}$-cycloalk(en)yl-$C_{1-6}$-alk(en/yn)yl;

$R^8$-$R^{11}$ are independently selected from the group consisting of hydrogen, halogen, cyano, $C_{1-6}$-alk(en/yn)yl, $C_{3-8}$-cycloalk(en)yl, $C_{3-8}$-cycloalk(en)yl-$C_{1-6}$-alk(en/yn)yl, halo-$C_{1-6}$-alk(en/yn)yl, halo-$C_{3-8}$-cycloalk(en)yl, halo-$C_{3-8}$-cycloalk(en)yl-$C_{1-6}$-alk(en/yn)yl, nitro, amino, $C_{1-6}$-alk(en/yn)ylamino, di-($C_{1-6}$-alk(en/yn)yl)amino, $C_{3-8}$-cycloalk(en)ylamino, $C_{3-8}$-cycloalk(en)yl-$C_{1-6}$-alk(en/yn)ylamino, hydroxy, $C_{1-6}$-alk(en/yn)yloxy, $C_{3-8}$-cycloalk(en)yloxy, $C_{3-8}$-cycloalk(en)yl-$C_{1-6}$-alk(en/yn)yloxy, $C_{1-6}$-alk(en/yn)ylsulfanyl, $C_{3-8}$-cycloalk(en)ylsulfanyl and $C_{3-8}$-cycloalk(en)yl-$C_{1-6}$-alk(en/yn)ylsulfanyl;

m+n+o+p equals to 1, wherein m, n, o, and p are independently 0 or 1;

X is selected from the group consisting of $CH_2$, $CHR^{12}$ and $CR^{13}R^{14}$;

Y is selected from the group consisting of $CH_2$, $CHR^{15}$ and $CR^{16}R^{17}$;

Z is selected from the group consisting of $CH_2$, $CHR^{18}$ and $CR^{19}R^{20}$; and Q is selected from the group consisting of $CH_2$, $CHR^{21}$ and $CR^{22}R^{23}$;

wherein $R^{12}$-$R^{23}$ are independently selected from the group consisting of $C_{1-6}$-alk(en/yn)yl, $C_{3-8}$-cycloalk(en)yl and $C_{3-8}$-cycloalk(en)yl-$C_{1-6}$-alk(en/yn)yl;

or a pharmaceutically acceptable salt thereof.

2. The compound according to claim 1, wherein $R^1$ and $R^2$ are independently hydrogen or $C_{1-6}$-alk(en/yn)yl; or $R^1$ and $R^2$ together with the nitrogen to which they are attached form a 4-7 membered ring containing zero or one double bond, optionally said ring in addition to said nitrogen comprises one further heteroatom selected from the group consisting of oxygen and sulphur.

3. The compound according to claim 1, wherein $R^3$-$R^6$ are independently selected from the group consisting of hydrogen, halogen and $C_{1-6}$-alk(en/yn)yl.

4. The compound according to claim 1, wherein $R^7$ is hydrogen or $C_{1-6}$-alk(en/yn)yl.

5. The compound according to claim 1, wherein $R^8$-$R^{12}$ are independently selected from the group consisting of hydrogen, halogen, $C_{1-6}$-alk(en/yn)yl, di-($C_{1-6}$-alk(en/yn)yl)amino, hydroxy and $C_{1-6}$-alk(en/yn)yloxy.

6. The compound according to claim 1, wherein X, Y, Z and Q are $CH_2$.

7. A pharmaceutical composition comprising a compound according to claim 1 and at least one pharmaceutically acceptable carrier or diluent.

8. A method for treating a subject suffering from a disorder or disease comprising administering to the subject a therapeutically effective amount of a compound according to claim 1, wherein the disorder or disease is treated by the inhibition of the serotonin transporter, and wherein the disorder or disease is selected from the group consisting of depressive disorder, anxiety disorder, pain disorder, attention deficit hyperactivity disorder, and stress urinary incontinence.

9. The method of claim 8, wherein the disorder or disease is a depressive disorder.

10. The method of claim 9, wherein the depressive disorder is selected from the group consisting of major depressive disorder, postnatal depression, dysthymia or depression associated with bipolar disorder, depression associated with Alzheimer's disease, depression associated with psychosis and depression associated with Parkinson's disease.

11. The method of claim 8, wherein the disorder or disease is an anxiety disorder.

12. The method of claim 9, wherein the anxiety disorder is selected from the group consisting of general anxiety disorder, social anxiety disorder, post traumatic stress disorder, obsessive compulsive disorder, panic disorder, panic attacks, specific phobias, social phobia and agoraphobia.

13. The method of claim 8, wherein the disorder or disease is a pain disorder.

14. The method of claim 13, wherein the pain disorder is selected form a group consisting of fibromyalgia syndrome, overall pain, back pain, shoulder pain, and headache.

15. The method of claim 13, wherein the pain disorder occurs while awake and during daily activities.

16. The method according to claim 8, wherein the disorder or disease is attention deficit hyperactivity disorder.

17. The method according to claim 8, wherein said disorder or disease is stress urinary incontinence.

18. The compound of claim 1, selected from the group consisting of:

[2-(Benzo[b]thiophen-3-ylsulfanyl)-benzyl]-methyl-amine;

Methyl-[2-(2-methyl-benzo[b]thiophen-3-ylsulfanyl)-benzyl]-amine;

[2-(5-Fluoro-benzo[b]thiophen-3-ylsulfanyl)-benzyl]-methyl-amine;

Methyl-[2-(5-methyl-benzo[b]thiophen-3-ylsulfanyl)-benzyl]-amine;

[2-(5-Chloro-benzo[b]thiophen-3-ylsulfanyl)-benzyl]-methyl-amine;

[2-(Benzo[b]thiophen-3-ylsulfanyl)-benzyl]-dimethyl-amine;

[2-(Benzo[b]thiophen-3-ylsulfanyl)-5-methyl-benzyl]-methyl-amine;

[2-(Benzo[b]thiophen-3-ylsulfanyl)-4-chloro-benzyl]-methyl-amine;

[2-(4-Fluoro-benzo[b]thiophen-3-ylsulfanyl)-benzyl]-methyl-amine;

Dimethyl-[3-(2-methylaminomethyl-phenylsulfanyl)-benzo[b]thiophen-5-yl]-amine;

Methyl-[2-(7-methyl-benzo[b]thiophen-3-ylsulfanyl)-benzyl]-amine;

[2-(4,7-Dimethyl-benzo[b]thiophen-3-ylsulfanyl)-benzyl]-methyl-amine;

3-(2-Methylaminomethyl-phenylsulfanyl)-benzo[b]thiophen-5-ol;

Methyl-[2-(6-methyl-benzo[b]thiophen-3-ylsulfanyl)-benzyl]-amine;

[2-(7-Methoxy-benzo[b]thiophen-3-ylsulfanyl)-benzyl]-methyl-amine;

{2-[2-(Benzo[b]thiophen-3-ylsulfanyl)-phenyl]-ethyl}-methyl-amine;

{3-[2-(Benzo[b]thiophen-3-ylsulfanyl)-phenyl]-propyl}-methyl-amine;

{4-[2-(Benzo[b]thiophen-3-ylsulfanyl)-phenyl]-butyl}-methyl-amine;

2-(Benzo[b]thiophen-3-ylsulfanyl)-benzylamine;

4-[2-(Benzo[b]thiophen-3-ylsulfanyl)-benzyl]-morpholine; and

4-[2-(Benzo[b]thiophen-3-ylsulfanyl)-benzyl]-thiomorpholine;

or a pharmaceutically acceptable salt thereof.

* * * * *

UNITED STATES PATENT AND TRADEMARK OFFICE
CERTIFICATE OF CORRECTION

PATENT NO. : 7,534,791 B2  Page 1 of 1
APPLICATION NO. : 11/452823
DATED : May 19, 2009
INVENTOR(S) : Jan Kehler et al.

It is certified that error appears in the above-identified patent and that said Letters Patent is hereby corrected as shown below:

Column 37, lines 54-58,

"12. The method of claim 9, wherein the anxiety disorder is selected from the group consisting of general anxiety disorder, social anxiety disorder, post traumatic stress disorder, obsessive compulsive disorder, panic disorder, panic attacks, specific phobias, social phobia and agoraphobia."

should read

-- 12. The method of claim 11, wherein the anxiety disorder is selected from the group consisting of general anxiety disorder, social anxiety disorder, post traumatic stress disorder, obsessive compulsive disorder, panic disorder, panic attacks, specific phobias, social phobia and agoraphobia. --

Signed and Sealed this

Twenty-eighth Day of July, 2009

JOHN DOLL
*Acting Director of the United States Patent and Trademark Office*